United States Patent [19]

Wheeler, deceased et al.

[11] Patent Number: 5,351,698
[45] Date of Patent: Oct. 4, 1994

[54] BIDIRECTIONALLY DONNABLE GENERALLY TUBULAR SHEATH ARTICLES, AND APPARATUS AND METHOD FOR MAKING AND USING SAME

[75] Inventors: Robert G. Wheeler, deceased, late of Greenbank, Wash., by Helen J. Wheeler, legal representative; Edwin C. White, Jr., Siler City, N.C.

[73] Assignee: Family Health International, Research Triangle Park, N.C.

[21] Appl. No.: 861,646

[22] Filed: Apr. 1, 1992

Related U.S. Application Data

[60] Continuation-in-part of Ser. No. 726,984, Jul. 8, 1991, abandoned, which is a division of Ser. No. 568,426, Aug. 16, 1990, Pat. No. 5,036,863, which is a division of Ser. No. 271,884, Nov. 15, 1988, Pat. No. 4,964,416, and a continuation-in-part of Ser. No. 775,783, Oct. 11, 1991, Pat. No. 5,335,675, which is a continuation-in-part of Ser. No. 726,984, Jul. 8, 1991, abandoned, which is a continuation-in-part of Ser. No. 568,426, Aug. 16, 1990, Pat. No. 5,036,863, which is a division of Ser. No. 271,884, Nov. 15, 1988, Pat. No. 4,964,416.

[51] Int. Cl.⁵ ............................................. A61F 6/02
[52] U.S. Cl. ................................. 128/844; 128/918
[58] Field of Search .................... 128/842, 844, 918; 604/330, 347–353

[56] References Cited

U.S. PATENT DOCUMENTS

| | | |
|---|---|---|
| D. 253,009 | 9/1979 | Okamoto . |
| 1,113,561 | 10/1914 | Jorgenson . |
| 2,285,981 | 6/1942 | Johns . |
| 2,305,453 | 12/1942 | Martos . |
| 2,389,831 | 11/1945 | Welsh . |
| 2,410,460 | 11/1946 | Robinson . |
| 2,433,538 | 12/1947 | Warner . |
| 2,484,356 | 10/1949 | Ribeiro et al. . |
| 2,488,938 | 9/1950 | Wayne . |
| 2,577,345 | 12/1951 | McEwen . |
| 2,586,674 | 2/1952 | Lonne . |
| 2,591,783 | 4/1952 | Craddock ........................... 128/842 |
| 2,604,092 | 7/1952 | Brown et al. . |
| 2,670,736 | 3/1954 | Dunkelberger . |
| 2,705,951 | 4/1955 | Crowner ............................. 128/844 |
| 2,904,041 | 9/1959 | Brown . |
| 3,037,508 | 6/1962 | Freidman . |
| 3,136,417 | 6/1964 | Clinch ................................ 128/844 |
| 3,149,017 | 9/1964 | Ehririch et al. . |
| 3,295,145 | 1/1967 | Erickson . |
| 3,361,857 | 1/1968 | Maddison . |
| 3,559,651 | 2/1971 | Moss . |

(List continued on next page.)

FOREIGN PATENT DOCUMENTS

| | | |
|---|---|---|
| 0147072 | 7/1985 | European Pat. Off. . |
| 2020280 | 11/1971 | Fed. Rep. of Germany . |
| 2349361 | 4/1975 | Fed. Rep. of Germany . |
| 1595711 | 8/1981 | United Kingdom . |

*Primary Examiner*—Michael A. Brown
*Attorney, Agent, or Firm*—Steven J. Hultquist

[57] ABSTRACT

An article having a main sheath portion formed of a flexible and/or elastic material closed at a distal end thereof and open at a proximal end thereof, with a first flange element formed of a flexible and elastic material, and having an aperture formed or pressure-formable therein, secured to the open proximal end of the sheath. In a single flange embodiment, the main sheath portion may be provided in a center-compacted configuration, for bidirectional application of the sheath. In a multi-flange embodiment, a second flange element is secured at an outer portion thereof to the first flange element and has an aperture formed or pressure-formable therein, in substantial alignment with the aperture of the first flange element, whereby the sheath is extended or extensible from a compacted state through the aperture in either the first or the second flange element. In a specific embodiment, the article comprises a condom which may be donned in either of two directions. Such bidirectionally donnable condom article is characterized by ease of use and improved safety and reliability, as compared to prior art condoms.

33 Claims, 15 Drawing Sheets

U.S. PATENT DOCUMENTS

| | | | |
|---|---|---|---|
| 3,588,997 | 6/1971 | Field . | |
| 3,759,254 | 9/1973 | Clark . | |
| 3,992,766 | 11/1976 | Field . | |
| 4,004,591 | 1/1977 | Freimark . | |
| 4,009,717 | 3/1977 | Allen . | |
| 4,022,213 | 5/1977 | Stein | 604/350 |
| 4,100,309 | 7/1978 | Micklus . | |
| 4,232,675 | 11/1980 | Meldahl . | |
| 4,241,828 | 12/1980 | Bourdelle et al. . | |
| 4,275,812 | 6/1981 | Poncy . | |
| 4,354,494 | 10/1982 | Hogan . | |
| 4,432,357 | 2/1984 | Pomeranz . | |
| 4,446,860 | 5/1984 | Gutnick . | |
| 4,475,910 | 10/1984 | Conway et al. . | |
| 4,484,918 | 11/1984 | Omley . | |
| 4,576,156 | 3/1986 | Dyke . | |
| 4,588,397 | 5/1986 | Giacalone | 604/351 |
| 4,626,250 | 12/1986 | Schneider . | |
| 4,664,104 | 5/1987 | Jaicks | 604/353 |
| 4,684,490 | 8/1987 | Taller et al. . | |
| 4,735,621 | 4/1988 | Hessel . | |
| 4,781,709 | 11/1988 | Grubman . | |
| 4,794,929 | 1/1989 | Robichaud . | |
| 4,795,425 | 1/1989 | Pugh . | |
| 4,798,600 | 1/1989 | Meadows . | |
| 4,805,604 | 2/1989 | Spery . | |
| 4,808,174 | 2/1989 | Sorkin . | |
| 4,834,113 | 5/1989 | Reddy | 604/353 |
| 4,834,114 | 5/1989 | Boarman . | |
| 4,872,464 | 10/1989 | Loeb et al. . | |
| 4,875,490 | 10/1989 | Quiroz . | |
| 4,875,491 | 10/1989 | Parrone | 604/349 |
| 4,885,169 | 12/1989 | McGlothin et al. . | |
| 4,888,007 | 12/1989 | Loeb et al. . | |
| 4,942,885 | 7/1990 | Davis et al. . | |
| 4,955,392 | 9/1990 | Sorkin . | |
| 4,964,416 | 10/1990 | Foldesy et al. . | |
| 4,966,166 | 10/1990 | Leffler . | |
| 4,993,433 | 2/1991 | Reddy . | |
| 5,036,863 | 8/1991 | Wheeler | 128/844 |

BIDIRECTIONALLY DONNABLE GENERALLY TUBULAR SHEATH ARTICLES, AND APPARATUS AND METHOD FOR MAKING AND USING SAME

CROSS-REFERENCE TO RELATED APPLICATIONS

This is a continuation-in-part of U.S. application Ser. No. 07/726,984 filed Jul. 8, 1991, now abandoned, which is a divisional application of U.S. application Ser. No. 07/568,426 filed Aug. 16, 1990, and issued Aug. 6, 1991 as U.S. Pat. No. 5,036,863, which in turn is a divisional application of U.S. application Ser. No. 07/271,884 filed Nov. 15, 1988 and issued Oct. 23, 1990 as U.S. Pat. No. 4,964,416. This application is also a continuation-in-part of U.S. application Ser. No. 07/775,783 filed Oct. 11, 1991, now U.S. Pat. No. 5,335,675, which in turn is a continuation-in-part of U.S. application Ser. No. 07/726,984 filed Jul. 8, 1991, now abandoned, which in turn is a continuation-in-part of U.S. application Ser. No. 07/568,426 filed Aug. 16, 1990 and issued as U.S. Pat. No. 5,036,863, which in turn is a division of U.S. application Ser. No. 07/271,884 filed Nov. 15, 1988 and issued as U.S. Pat. No. 4,964,416.

BACKGROUND OF THE INVENTION

1. Field of the Invention

The present invention generally relates to flanged, generally tubular articles, including bidirectionally donnable multiple flange condom articles, and to method and apparatus for making and using such articles.

2. Description of the Related Art

In recent years, there has been a significant increase in the incidence and spread of sexually transmitted diseases, and this phenomenon has in turn caused an increased use of condoms as a prophylactic measure to reduce the risk of infection and transmission of such diseases.

Among the reasons for the increase in incidence and rate of transmission of sexually transmitted diseases (STDs) are the development of increasingly antibiotic-resistant strains of disease-causing organisms, e.g., those responsible for diseases such as syphilis and gonorrhea. Another factor has been the absence of any effective cure for acquired immunodeficiency syndrome (AIDS).

Against the foregoing background, and the recognition that condoms afford a safe, low cost, and generally reliable means for combatting the spread of STDs including AIDS, there has been an increased demand for condoms.

Currently, most condoms are produced from a latex resin via a dipping process in which a cylindrical and rounded-end mold is dipped into a resin bath, so that the mold is coated with a thin layer of the latex material. The thickness of the latex coating on the mold is dependent on the viscosity of the latex, and the speed of extracting the mold from the latex bath. Similar latex dipping processes have been employed with suitably shaped molds to form tight-fitting gloves such as surgical gloves.

The above-described latex dipping process has been utilized for decades, and yields a generally satisfactory barrier product at reasonable cost.

With the recent spread of AIDS in the general population and the resurgence of condom usage in sexual activities, there has been interest in improving the strength and reliability characteristics of condoms, and of achieving improvements in manufacturing processes and economics, to further combat the spread of STDs generally, and AIDS specifically, as well as to provide a safe, reliable, and convenient contraceptive means. In this respect, there is a continuing need to provide condoms in a readily packaged form. The packaging itself should ensure the physical integrity, safety, and effectiveness of the condom are maintained. The package and the condom should be designed in a manner facilitating ready removal and use of the condom, in order to enhance the appeal of using condoms in coital activity.

U.S. Pat. No. 4,576,156, issued Mar. 18, 1986 to Manfred F. Dyke, discloses a condom formed of a thermoplastic polyurethane material, having a generally cylindrical configuration with an open proximal end and a closed distal end. The disclosed condom has a thickness of from about 0.01 millimeters, or less, to about 0.25 millimeters. The thermoplastic polyurethane employed to form the condom is disclosed as having: an average Shore A hardness of from about 50 to about 90; a tensile stress, at 100% of elongation, between about 300 and 1,000 psi; and a tensile stress, at 300% elongation, between about 800 and 3,000 psi. Suitable thermoplastic polyurethane species for manufacturing the condom include those set out at column 2, line 55 to column 3, line 10 of the Dyke patent, with polyether- or polyester-based urethane elastomer said to be preferred. In the manufacture of the thermoplastic polyurethane condom disclosed in the Dyke patent, a film of the polyurethane material, e.g., in the form of a 6-inch square, is heated to a temperature high enough to soften the polymer but low enough to avoid chemical degradation, preferably in a clamping frame, and at a temperature of about 400°–500° F. The heated film then is brought into contact with a preformed mandril to cause the film to assume the shape of the mandril, preferably with application of a vacuum to the system in order to bring about uniformity in wall thickness (column 3, lines 47–50 of the patent).

European patent application 0 147 072, published Jul. 3, 1985, in the names of Robert A. Taller, et al, discloses a process for making a polyurethane condom with a uniform thickness of from about 1.5 to about 4 mils. A heat-curable polyurethane prepolymer solution is employed into which a mold is dipped and withdrawn for heat curing on the mold. The polyurethane prepolymer which is employed in the dipping medium is the reaction product of a polyisocyanate and with at least one long chain polyol. The polyol is amorphous at room temperature, has an average molecular weight of from about 500 to about 5,000, and a hydroxyl number of from 225 to about 22.4. The polyurethane prepolymer has a NCO/OH ratio of from about 0.95:1 to about 1.1:1.

U.S. Pat. No. 4,009,717 to C. H. Allen discloses a condom comprising inner and outer sheaths, with the inner-sheath volume providing a fluid reservoir so that the interior of the inner sheath remains dry. The outer sheath is closed at one end and open at the other. The inner sheath is open at both ends inside the outer sheath, with means between the inner and outer sheath establishing a fluid-tight seal to form the fluid reservoir therebetween.

U.S. Pat. No. 4,955,392 to R. Sorokin discloses a condom formed of elastomeric film material and including a tubular length having a closed distal end and a proximal open end with an integral pubic shield about the proximal open end.

U.S. Pat. No. 4,232,675 to E. N. Meldahl discloses a modified condom of shorter length than conventionally employed, interiorly containing a spermicidal ring and a penis-supported harness assembly.

Various condom designs have evolved which feature a double-walled chamber at the distal end of the condom containing contraceptive or medicant material. Examples include U.S. Pat. No. 4,332,243 to M. Gutnick; U.S. Pat. No. 2,410,460 to J. P. Robinson; U.S. Pat. No. 4,446,860 to M. Gutnick; and U.S. Pat. No. 2,577,345 to F. L. McEwen.

West German Offenlegungsschrift 2020280 discloses a condom comprising two sheaths inserted in each other, the inner sheath having an opening through which semen can discharge and be fastened in place by two rubber rings.

U.S. Pat. No. 2,433,538 to H. W. Warner discloses a semen receptacle article having a removable container therein. The container has a distal receiver opening and contains absorbent material for receiving and absorbing a sperm specimen. It appears from the description that the receptacle member is placed on the male organ with the distal end of the penis in the vicinity of the proximal wall of the sperm container, but not inserted through the sperm container opening.

U.S. Pat. No. 2,586,674 to F. Lonne describes a prophylactic construction (see FIG. 3 of the patent, and appertaining description at column 2, lines 26–36) wherein a double-layer condom comprises an inner pellicle having annular projections or extensions transverse to the longitudinal dimension of the prophylactic.

U.S. Pat. No. Design 253,009 to T. Okamoto shows a prophylactic device whose frontal (distal) section comprises a pair of indented surface portions forming circumferential grooves in the prophylactic, transverse to the longitudinal axis thereof.

U.S. Pat. No. 3,295,145, to R. E. Erickson describes a urine collector for infants, comprising front and rear panels sealed to one another to form a throat dividing the collector into upper and lower compartments. The back panel of the collector features an oval aperture surrounded by a pressure-sensitive adhesive for adhering the collector to the infant's skin. The collector panels preferably are formed of a substantially transparent thermoplastic film such as polyethylene, vinyl copolymers and the like, at a thickness of from about 0.5 to 3 mils.

U.S. Pat. No. 4,022,213, to D. Stein discloses a male drip urinal comprising a tubular sleeve including a thin rubber sheath which is stretched over the penis for sealing purposes. An apertured resilient sheet extends across the mouth of the urinal sleeve for sealing about the base of the penis, to provide a backup seal should the inner sheath tear. The sheet is carried by an annular ring forming the mouth of the urinal sleeve.

U.S. Pat. No. 2,448,938, to A. Wayne describes a sanitary protective appliance which may be configured with a shield-like body portion of slightly convex shape in side elevation view, with an accordion-like finger portion which is foldable back against the convex face of the body portion. The finger portion is convergingly shaped from its proximal to its distal end portions. The body portion of this device contains a generally central opening forming a passage into the finger portion and comprises an integral tab to facilitate removal of the appliance after use. The rear (proximal) face of the body portion is peripherally coated with an adhesive coating material, except for the tab. The adhesive coating is overlaid with a gauze cover which is removable to affix the appliance, for covering or protecting a body appendage.

U.S. Pat. No. 4,735,621, to L. Hessel discloses a tubular protective condom-like device comprising a flexible, thin-walled tube closed at one end and having its opposite open end a collar-shaped, outwardly extending portion with means for radially stretching the collar or open end. In one disclosed embodiment, the device has a first outwardly extending ring-shaped means adapted for radially extending the open end, and a second outwardly extending ring-shaped means adapted for radially extending the open end, and a second outwardly extending ring-shaped means that is adapted for radially extending the closed end. The second ring-shape means thus secures or maintains the device in the vagina in a manner similar to a diaphragm.

U.S. Pat. No. 4,964,416 to Robert G. Wheeler discloses a condom having a main sheath portion closed at a distal end and open at a proximal end thereof, which may be constructed from thermoplastic elastomeric materials. The condom also has an annular-shaped sealing element, formed of an elastic material, circumscribing an interior opening of smaller size than the proximal end opening of the condom, and joined at the outer periphery of the sealing element to the main sheath, at or in the vicinity of the proximal end opening. Such construction thereby provides a barrier member in the proximal segment of the condom to enhance its effectiveness as a contraceptive and to minimize the incidence of sexually transmitted diseases.

U.S. Pat. No. 4,834,113 to A. V. K. Reddy discloses a prophylactic device to be worn by a recipient coital party, which utilizes a rolled-up pouch portion as a body cavity entry guide. As such the device can only be oriented upon the wearer's body in one direction for proper use.

U.S. Pat. No. 4,415,548 to A. V. K. Reddy discloses a spermicidally-active lubricated prophylactic, having a spermicidally active lubricant on both sides of the condom.

There are, however, several deficiencies which still need to be addressed and which would provide a major improvement in condom articles. These include: air entrapment caused by donning an unfurled (i.e., non-rolled, such as a natural skin) condom: the friction or "drag" associated with donning an unfurled condom; acceptable, comfortable aperture size; the necessity of having the correct side of previously rolled or slip-on condoms contact the penis, in order for donning to be successful; and the need for greater ease of handling the condom while donning.

In respect of the "correct side" deficiency noted above, this characteristic is particularly applicable to rolled condoms which are "rolled up" along the entire length of the sheath to yield a fully rolled product of generally flat configuration in which the distal end portion of the sheath is surrounded by a toroidal ring constituted by the rolled sheath material. When such rolled condom is removed from its package, particularly in a low-light or dark environment, it frequently occurs that the condom is applied to the tip of the glans in a "wrong facing" orientation, such that it is not able to be unrolled on the penis by manually urging the roll downwardly over the shaft of the penis. The user, upon discerning such wrong orientation, then flips the rolled condom over and properly applies it to the penis, but in such process, the surface of the condom film initially contacting the glans is externally exposed on the condom as finally installed. This may result in transmission of sexually transmittable disease and/or sperm to the recipient coital partner, whereby the contraceptive and disease-protective functions of the condom are compromised.

Even in a fully illuminated environment, inexperienced condom users frequently initially position rolled condoms on the penis in a "wrong side up" orientation.

Accordingly, it is an object of the present invention to provide improved flanged tubular articles, e.g., condoms, which are readily, simply, and inexpensively formed.

It is another object of the present invention to provide improved condom articles which substantially eliminate air entrapment, reduce friction associated with donning of the condom article, eliminate the "one right side" feature of previous condoms, and provide simpler handling and greater ease of use, as compared to conventional condoms.

A further object of the present invention is to provide an acceptable, comfortable aperture size in the condom article, which is absent in prior art flanged condom articles.

It is another object of the invention to provide apparatus and methods for making and using condoms of the aforementioned type.

Other objects and advantages of the present invention will be more fully apparent from the ensuing disclosure and appended claims.

SUMMARY OF THE INVENTION

In a broad article aspect, the present invention relates to an article comprising a main sheath portion having an elongate form when fully extended, with a closed distal end and an open proximal end. A first flange element is secured to the open proximal end of the main sheath and has an aperture formed or pressure-formable in the flange element, in general registration with the proximal open end of the sheath. A second flange element is secured at an outer peripheral portion thereof to the first flange element. The second flange element has an aperture formed or pressure-formable therein, in general registration with the aperture of the first flange element. In this article, the main sheath is compactible to a compacted form which is able to be reposed between the first and second flange elements.

The compacted form of the article may constitute a rolled form, wherein the sheath is rolled into a compacted state comprising a toroidal or circular roll, e.g., of the type characteristic of conventional rolled condoms. Alternatively, the compacted form may comprise a compressed or otherwise compacted shirred sheath confirmation, or the sheath may otherwise be compacted in any suitable manner, as for example by simple gathering and compaction, zig-zag folding, accordion-folding, or other folding or alternative methods by which the sheath is rendered to a conformation of compacted character.

As used herein, the term "pressure-formable" in reference to apertures of the flange element(s) of the invention, means apertures which may be readily formed, of a predetermined size and shape, by pressure of the body part or structure to be sheathed, against the flange element in which the aperture is desired. A flange element may be provided with a pressure-formed aperture, for example, by providing a weakened region in the flange element such as a serrated cut line, or a reduced thickness of material at the intended periphery of the aperture opening, which will yield to pressure of the body part or structure thereagainst, to provide the desired opening. As a further specific example, a flange element, in condom usage of the article of the present invention, featuring pressure-formable aperture openings in the flange element(s), may feature a series of concentric rings defining a corresponding series of serrated-cut "punch-outs", so that the application of the condom to the erect penis will punch-out the appropriate serrated circle and associated disk of material, to accommodate the particular size of the penis being sheathed by the condom article.

A particularly preferred compacted state of the sheath in the article of the invention is a center-compacted state. As used herein, the term "center-compacted" means that the sheath of the inventive article is partially everted (turned inside out) so that a section of the length of the sheath is disposed inside the remaining segment of the sheath length, following which the sheath comprising such reentrant sheath structure is compacted to a compacted state. Preferably, the center-compacted configuration includes a distal segment of the sheath being re-entrantly inserted into the remaining, proximal segment of the sheath, prior to the further compaction thereof, e.g., by rolling, folding, gathering, or otherwise achieving a final compacted state.

In association with a flange element joined to the proximal open end of the sheath, such center-compacted configuration permits the distal end of the sheath to be placed in proximity to, and in general registration, with the (formed or pressure-formable) aperture of the flange element. In this manner, the sheath is particularly advantageously applied to the body part or structure (element or article to be sheathed), in either of two opposing directions, so that the sheath is "bi-directionally donnable" or "bi-directionally applicable" in character.

In another broad aspect, the present invention relates to an article comprising a main sheath having an elongate form when fully extended, with a closed distal end and an open proximal end, with a flange element secured to the open proximal end of the main sheath and having an aperture formed or pressure-formable in the flange element, in general registration with the open proximal end of the sheath. The main sheath is in a center-compacted configuration against the flange element, with the distal end of the center-compacted main sheath in general registration with the aperture of the flange element. This article, comprising a center-compacted sheath secured at its proximal end to a flange element, provides bi-directional donnability/applicability in use of the article.

In the broad practice of the present invention, the main sheath employed in the inventive article may be of any suitable size and specific shape. For example, the main sheath may be of a cylindrical tubular form, or alternatively it may have a baggy configuration. The specific confirmation of the sheath will be readily determinable by those skilled in the art, in application to a particular end use.

In another, specific aspect, the present invention relates to an article comprising a generally tubular main sheath having a closed distal end and an open proximal end. The sheath is of generally tubular shape in an unrolled or uncompacted configuration, and is rolled or rollable into a toroidal-shaped roll surrounding a distal end portion of the sheath, or is otherwise compacted or compactible to a compacted state. The sheath is formed of a flexible and/or elastic material, with a first flange element formed of a flexible and elastic material, the first flange element being centered over the open proximal end of the main sheath and secured thereto, with a central aperture in the first flange element. A second flange element formed of a flexible and elastic material is positioned in facing relationship to the first flange element and is secured to the first flange element, with a central aperture in the second flange element and in general registration with the central aperture in the first flange element. The first and second flange elements are secured so as to allow the sheath when rolled or otherwise compacted, to repose between the first and second flange elements (with the sheath in a rolled or otherwise compacted form), with the distal end portion of the sheath in general registration with the aperture openings in the first and second flange elements, and with the sheath being selectively extendable from a compacted form in a selected one of alternative directions comprising in a first direction the sheath when extended, passing through the aperture in the first flange element and comprising in a second direction the sheath when extended, passing through the aperture in the second flange element.

The main sheath and flange elements may independently be formed of any suitable material or materials (i.e., the sheath and respective flange elements may be formed of a same material of construction or each may be formed of differing materials from the other such components). Examples of materials which may find utility in the broad practice of the present invention as fabrication materials for the main sheath and respective flange elements include: natural as well as synthetic rubbers, e.g., latex; natural skin materials; and synthetic plastic, and/or elastic materials, such as thermoplastic materials and most preferably thermoplastic elastic materials.

The tubular article may comprise diametrically-opposed heat seals extending longitudinally along the main sheath and converging at the distal end of the main sheath. The first flange element may be joined to the main sheath portion at the proximal part thereof by any suitable means and/or method of securement, sealing, or attaching, and the second flange element may likewise be secured to the first flange element by any suitable securing means and/or method.

The tubular articles of the present invention may be employed in a wide variety of end use applications and for varying purposes. Tubular articles of the invention may for example be employed as finger cots, tubular bandages, condoms, gloves, mittens, or other hand coverings, as well as shoe coverings, leg warmers, etc. The specific application will of course determine the materials of construction which advantageously are employed, such as woven or non-woven fabrics, natural or synthetic rubbers, synthetic polymeric film materials, etc.

In a preferred aspect, the tubular article of the invention is employed as a condom for the purpose of contraception and/or providing a means of reducing the risk of transmission of sexually transmitted diseases.

In another aspect, the present invention relates to a condom article as generally described hereinabove, wherein a cavity formed by the securement of the first and second flange elements to one another contains the main sheath portion of the condom in a compacted form, e.g., a toroidal-shaped roll of the main sheath, in rolled condition. The cavity may suitably have disposed therein a lubricant, spermicide, medicament, other filling material, or mixtures of two or more of the foregoing components.

The tubular articles of the present invention may be formed by any suitable method of manufacture, including dipping, thermoforming, blow-extrusion, heat-sealing of preformed film stock, or in any other suitable manner.

Other aspects of the invention include apparatus and method for manufacturing articles of the type broadly described hereinabove.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
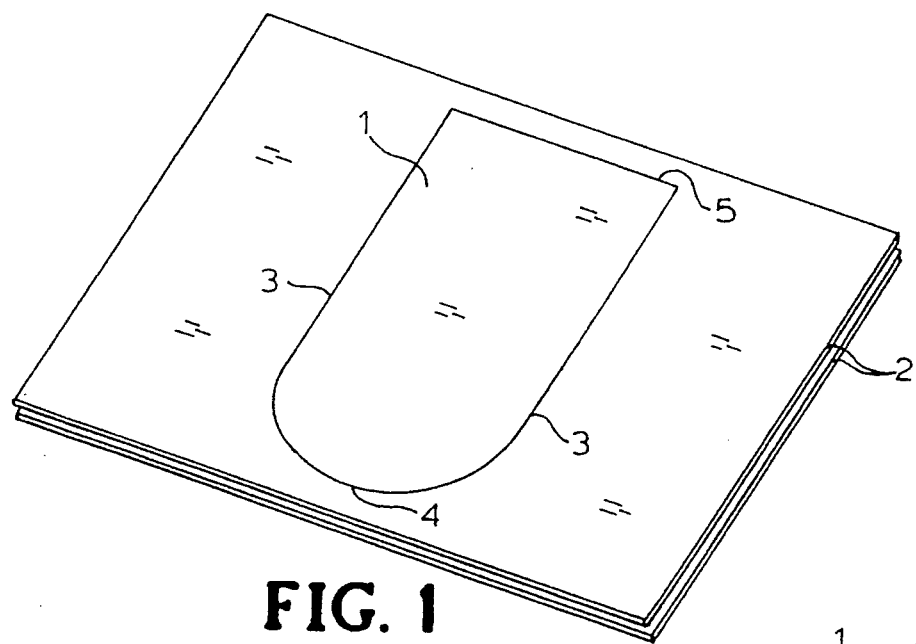
FIG. 1 is a perspective view of a tubular main sheath blank made from two flat sheets of material in substantial registration which are simultaneously cut and then heat-sealed continuously around both sides and the rounded end, leaving an open end thereto.

The article of the present invention is of a general type having a generally tubular main sheath portion, closed at a distal end and open at a proximal end thereof.

The article of the present invention may, as discussed hereinabove, be formed by any suitable means and/or method of manufacture, including formation of the tubular main sheath by methods such as dipping (in latex or a polymeric material solution or dispersion), extrusion, blow-forming, thermoforming, etc.

In one advantageous embodiment, the main sheath portion of the tubular article may suitably be formed by heat-sealing or otherwise joining sheets of suitable flexible and/or elastic material to one another to define the main sheath portion of the article.

As also discussed hereinabove, the component parts and portions of the tubular article of the present invention may be formed of any of a wide variety of suitable materials, with the choice of specific materials being determined by the end use and performance requirements of the article. Materials which may be usefully employed, depending on the end use application of the article, include fabrics such as woven and non-woven web materials, including melt-blown, spun-bonded, hydroentangled, and other non-woven web forms; natural membrane materials such as lamb caecum and other natural skins; natural as well as synthetic rubbers and other elastomers; and plastic and thermoplastic film materials, including non-elastomeric films of such type; and combinations, composites, and alloys of suitable materials from among the foregoing list.

For applications such as gloves, mittens, leg warmers, socks, and other apparel items, fabrics including woven and non-woven materials, as well as plastic film apparel materials such as nylon, polypropylene, and blends of natural and synthetic fibers, may be employed in applications such as finger cots, condoms, and surgical apparel, preferred materials of construction may include latex rubber, thermoplastic elastic films, and the like.

In a preferred aspect, the main sheath of the article as usefully employed in condom applications may be formed by superposing corresponding sheets of a thermoplastic elastic material, and heat-sealing and severing same to form the tubular main sheath portion with a closed distal end and an open proximal end. Thus, the sheath of the article so formed will have perimetral edges which are heat-sealed in the desired configuration, e.g., with a surface profile defining an elongated U-shape.

Articles according to the present invention may also advantageously be formed by blow-forming the tubular main sheath portion of the article from a suitable thermoplastic material. As used herein, the term "blow-forming" is intended to be broadly construed to include (1) blow-extrusion forming, in which a tubular film of a thermoplastic material is extruded and a pressurized fluid introduced in its interior, typically an air "bubble", whose pressure and flow rate determines the dimensional characteristics of the blown tubular film, and (2) blow-molding, in which a tube of heated thermoplastic material is passed into an enclosing mold where a pressurized gas inside the tubular film expands the film into contact with the interior surfaces of the mold. The diameter of the tubular main sheath portion should of course be of a size commensurate with its intended use, e.g., in condom usage as a barrier means overfitting a penis.

The articles of the invention may comprise a main sheath of generally cylindrical shape. However, the specific structure of the sheath of the tubular article of the present invention may be widely varied, depending on the mode of application intended, and the specific materials of construction employed.

The materials which are particularly useful for forming condom articles of the invention include elastomeric materials, as well as flexible non-elastomeric materials such as nylons, polyethylene terephthalate, and olefinic homopolymers and copolymers, e.g., ultra-low density polyethylene.

As used herein, the term "elastomeric" in reference to thermoplastic materials useful for forming articles in accordance with the present invention, means a material which subsequent to elongation thereof under an applied tensional force, regains at least a significant portion of its original dimensional characteristics when the applied tensional force is released.

Illustrative of thermoplastic elastomeric materials which may find utility in the broad practice of the present invention are: polyurethane materials, as for example the polyester-based polyurethane material commercially available from Mobay Corporation (Plastics and Rubber Division, Pittsburgh, Pa.) under the trademark TEXIN ®, and the thermoplastic polyurethane elastomers which are commercially available from BASF Corporation (Parsippany, N.J.) under the trademark ELASTOLLAN ®; polyester elastomer, such as the block copolymers of polybutylene terephthalate and long-chain polyether glycols, which are available commercially from E. I. Du Pont de Nemours and Company, Inc. (Polymer Products Department, Engineering Polymers Division, Wilmington, Del.) under the trademark HYTREL ®; polyether blockamides, such as those commercially available from Atochem, Inc. (Glennrock, N.J.) under the trademark PEBAX ®; multiblock rubber-based copolymers, particularly those in which the rubber block component is based on butadiene, isoprene, or ethylene/butylene, such as those commercially available from Dow Chemical Company (Midland, Mich.) under the trademark ATTANE ®; as well as any other suitable homopolymers and copolymers, and mixtures, alloys, and composites thereof.

Among the foregoing materials, polyether- and polyester-based polyurethanes, and multiblock rubber-based copolymers are particularly preferred for forming condom articles according to the present invention. The most preferred materials for forming the condom articles in accordance with the present invention are the aforementioned thermoplastic polyurethane elastomers commercially available under the trademark ELASTOLLAN ® and blends thereof.

The composition of multiblock rubber-based copolymers employed as materials of construction for articles of the present invention may be varied widely, it being understood that the non-rubber repeating units of the copolymer may be derived from any suitable monomer(s), as for example, (meth)acrylate esters, such as methyl methacrylate, cyclohexylmethacrylate, etc.; vinyl arylenes, such as styrene; etc.

In general, the non-rubber blocks in the multiblock rubber-based copolymer preferably are derived from monomer(s) which are non-elastomeric in character, so that "soft" rubber blocks and "hard" non-elastomeric blocks are provided in the multiblock copolymer. Such hard blocks may suitably be derived from monomers of appropriate glass transition temperature (Tg) characteristics, with styrene being generally preferred. The rubber block of such multiblock copolymers may be formed of repeating units derived from synthetic rubbers such as butadiene, isoprene, ethylene/butylene, etc., with butadiene and ethylene/butylene elastomeric blocks generally being preferred.

The most preferred multiblock rubber-based copolymers are those having a A-B-A structure comprising polystyrene endblocks and an elastomeric midblock.

Illustrative multiblock butadiene-based copolymers which may be usefully employed in the broad practice of the present invention include those variously described in U.S. Pat. Nos. 3,297,793; 3,595,942; 3,402,159; 3,842,029; and 3,694,523, the disclosures of which hereby are incorporated by reference herein. Various multiblock styrene-containing polymers may be usefully employed to form the articles of the present invention. Examples of this type of polymer are triblock styrene-butadiene-styrene copolymers and styrene-ethylene/butylene-styrene terpolymers commercially available under the trademark KRATON from Shell Chemical Company (Houston, Tex.). Other examples of small block butadiene-styrene copolymers commercialized by Firestone Synthetic Rubber & Latex Company (Akron, Ohio) are marketed under the trademark STEREON.

In the general use of a multiblock rubber-based copolymer as the material of construction for the articles of the present invention or a constituent part of portion thereof, the copolymer material preferably is characterized by the following physical properties; a Shore A hardness of from about 30 to about 100; a tensile strength of from about 250 to about 4500 psi; and an ultimate elongation of from about 200% to about 1300%.

With reference to the use of polyurethanes as materials of construction for the articles of the present invention, preferred material characteristics include: a Shore A hardness from about 65 to about 100; an ultimate tensile strength from about 4,500 to about 10,000 psi; a tensile strength at 50% elongation of from about 400 to about 2,400 psi; an ultimate elongation of from about 350% to about 600%; and a tear strength of from about 300 to about 1,000 pli.

In the use of natural rubber as a material of construction in articles of the present invention, preferred material characteristics include tensile strength on the order of 3000 psi, elongation on the order of 700%, and tear strength on the order of 300 pli.

For natural skins as a material of construction for articles of the present invention, preferred material properties include a tensile strength wet value on the order of 1000 psi and a dry value on the order of 1500 psi; a 25% elongation in the wet or dry state; and a tear strength of 150 pli in wet condition and 220 pli in dry condition.

The various constituent parts of the articles of the present invention, i.e., the tubular main sheath, the first flange element, and the second flange element, may each be formed of different materials, or two or more of such constituent parts may be formed of a same material. Further, the various parts may be formed of different materials at different portions thereof, or otherwise utilize a multiplicity of material components in the fabrication of the article.

Concerning the various sheath-forming methods illustratively described hereinabove, it will be recognized that processing conditions and apparatus may be varied widely when blow-forming is utilized to form the tubular main sheath portions of articles in accordance with the present invention, depending on the specific thermoplastic material employed in the blow-forming operation, the volumetric space requirements of the process system, the method and apparatus employed for closure of the distal end of the tubular main sheath portion to form the finished sheath structure, etc. The choice of specific processing conditions, materials, and the like, may readily be determined for a given product application without undue experimentation, by those skilled in the art.

When blow-extrusion forming is employed to form the main sheath portion of the article, by way of example, the temperatures over a three-zone extruder may illustratively range from about 300° to about 380° F. for a polyester-based polyurethane material or a multiblock butadiene-based styrene copolymer, while the temperature range in the same extruder for an ultra-low density ethylene-octene copolymer or a polyether block amide may range from about 400° to about 450° F.; associated therewith are blow pressures which may range from 1 to 12 ounces per square inch of blown film, depending on the specific material employed.

When blow-extrusion is utilized as the method for blow-forming the tubular main sheath portion of the article, the resulting tubular sheath may have two open ends, and one of such open ends may then be closed to form the sheath of the article. The end closure operation may be carried out in any suitable manner, as for example by heat sealing, and preferably is automated so as to accommodate high speed manufacture of the ultimate product article in high volume. Thus, the tubular body formed by blow-extrusion may concurrently be sealed and severed at regular intervals along its length, to accommodate continuous processing.

The closure of the blow-extruded tubular main sheath portion preferably is carried out by heat-sealing, as this procedure is advantageous from the standpoint of thermoplastic materials being employed to form the product article.

The specific method of closure will depend largely on the specific material of construction employed for the tubular sheath portion of the article, as well as its thickness. The wall thickness of the sheath portion of the article may vary widely, but preferably is on the order of from about 0.01 to about 0.10 millimeter.

With such thicknesses, it is important that the sealing method not produce differential stresses or other material deficiencies in the tubular main sheath in the vicinity of the distal end seal. Accordingly, when heat-sealing is employed as a closure technique for forming the closed distal end of the condom, thermal impulse heat sealing is highly preferred, since it can initiate the sealing process at low temperature, with the material to be sealed thereafter quickly rising to the desired high sealing temperature, and then quickly returning to ambient temperature. Thus, rapid sealing of a localized region is effected in a manner which prevents nearby regions of the film being sealed from experiencing substantial temperature changes, such as might otherwise result in undesirable change of material properties in the vicinity of the seal. This consideration is particularly important in thinner films, e.g., with material thicknesses on the order of 0.05 millimeter, or lower, up to approximately 0.1 millimeter.

Thus, in a continuous process blow-extrusion system, wherein the blown film tube in continuously formed into discrete sheath articles, the sealing method may be combined with, or otherwise effect, severing of the film into discrete tubular segments for the desired product articles. For example, it may be possible to utilize an ultrasonic sealing assembly comprising an ultrasonic horn having associated therewith a blade element as an integral part of the horn structure, which in combination with a mating anvil effects concurrent or substantially contemporaneous severing of the tubular film into discrete sequential tubular segments and ultrasonic bonding of one of the distal ends thereof to form completed sheath members for the product articles. Alternatively, severing the tubular blow-extruded film to form discrete open-ended tubular main sheath portions, followed by a separate distal end-sealing operation, may be desirable.

In the broad practice of the present invention, the sheath may be formed from flat film stock or sheet material, which is folded and heat-sealed, or otherwise formed into the product article, or the main sheath portion thereof.

Dipping processes may likewise be employed to form the main sheath portion of articles of the present invention. In such processes, a mandril or other tubular form is provided and is dipped into a bath of latex resin or some other film-forming material such as a polymeric resin bath. The dipped mandril bearing the film-forming material is allowed to drain off excess material into the bath after its removal therefrom, and the coated mandril then may be placed in an elevated temperature environment, or other means to effect drying and/or curing of the applied wet film may be utilized, such as for example ultra-violet radiation exposure means, when the film-forming material is actinic radiation-curable in character.

As an alternative to such dipping processes, a mandril may be utilized which is sprayed with or otherwise has film-forming material applied thereto, following which the applied wet film is cured, such as hereinabove described.

Thermoforming processes also may be employed to form the tubular main sheath portion of the article of the present invention, in which heat and pressure may be employed to expand and/or shape a source material such as flowable liquid or a precursor film which then is subjected to expansion under thermoforming conditions.

It will be appreciated that a wide variety of conventional and commercially available processes may be employed to form the tubular main sheath portion of articles of the present invention, as is well known to those skilled in the art.

As discussed hereinabove, the sheath portions of the articles of the present invention may be formed in various configurations, including tubular or cylindrical-type configurations, the choice of a specific configuration depending on the particular materials of construction and the intended processing, packaging, and use environments of the article.

While the ensuing description herein of preferred embodiments of the present invention is directed to fabrication and structure of a condom article according to the present invention, it will be recognized that such description is intended for illustrative purposes only, and that the invention is broadly applicable to the provision of articles other than condoms, such as the various other article embodiments described hereinabove. Accordingly, the ensuing description is not to be limitingly construed, as regards the broad applicability of the present invention.

In the article of the invention, a first flange element, suitably formed of a flexible and elastic material, is disposed over the open proximal end of the main sheath and secured thereto, with a central opening in the flange element. Although the invention is hereinafter predominantly described with reference to a dual flange element condom construction, representing a highly preferred embodiment of the present invention, it will be recognized that single flange element structures, as well as multiple flange element structures having more than two flange elements, are comprehended within the broad scope of the present invention.

In condom applications, as well as in other uses (e.g., finger cots, and tubular bandages) wherein the tubular sheath is rolled onto a digit, extremity, or other member of the body, the flange element(s) serve as "tab(s)" or enhanced grippability structures facilitating the manual engagement and donning of the article.

In a single flange embodiment, the flange element may be employed, optionally with the assistance of a retainer structure, for donning. Alternatively, multiple flanges, including more than two flange elements, could be employed for sizing of the aperture in the first flange element, wherein multiple flanges could be constructed and arranged in a "peel-away" configuration so that different aperture openings are accommodated for sizing purposes to accommodate a specific digit, extremity, or member of the body.

When in a form comprising at least two flange elements, the present invention comprises, in addition to the aforementioned main sheath portion and first flange element, a second flange element formed of a flexible and elastic material (which as mentioned may be the same or different from the material of the first flange element). The second flange element is positioned in facing relationship to the first flange element, and is secured to such first flange element, with an aperture opening in the second flange element being in general registration with the aperture in the first flange element.

The first and second flange elements are secured to one another so as to allow the sheath, when rolled into a toroidal-shaped roll surrounding a distal end portion of the sheath, or when otherwise compacted, to be reposed between the facing first and second flange elements. In such "contained" configuration, the distal end portion of the sheath, when the sheath is in a center-compacted configuration, is in general registration with the aligned apertures in the first and second flange elements. In such fashion, the first and second flange elements form a pouch or container with an interior cavity communicating with the apertures defined by the respective first and second flange elements. Since the sheath in a rolled configuration comprises the distal end portion of the sheath surrounded by a toroidal roll, when the center-rolled sheath is positioned within the cavity, the sheath may be unrolled from either of two opposing directions along the general axis defined by the aligned aperture openings, by the simple expedient of inserting the digit, extremity, or other member of the body to be sheathed, against the distal end portion of the sheath within the cavity, so that the sheath is unrolled onto the body portion through the cavity aperture opening on the opposite side of the article from the aperture through which the digit, extremity, or member is first inserted to be sheathed.

Accordingly, the rolled sheath disposed within the containment structure defined by the first and second flange elements is selectively extendable in a selected one of alternative directions comprising, in a first direction, the sheath when applied extending through the aperture in the first flange element, and comprising, in a second direction, the sheath when applied extending through the aperture in the second flange element. Regardless of the direction of extension of the digit, extremity, or member of the body being sheathed, the body part becomes sheathed in a ready manner, avoiding binding, undue friction, and other characteristics and donning disadvantages which would increase the risk of damage to the overall article, or the sheath portion thereof.

Thus, the sheath is secured at a proximal end to one flange element, and such flange element (when at least two flange elements are employed) is secured in turn to a second flange element, wherein the apertures provided in the first and second flange elements are accommodated for extension (unrolling) of the main sheath in an extended position through either of the apertures of the respective flange elements, depending on the direction of extension of the body part through the flange element "package." By this construction, there is no "one right way" orientation, and in application to condom articles, the construction of the article of the invention obviates the difficulties and deficiencies of the rolled condoms of the prior art.

The flange elements employed in the invention may have any suitable shape, may have a significant radial extent, beyond the cross-section of the main sheath itself, and may in such "extended area" configurations have non-circular shapes, such as rectangular, elliptical, or any suitable polygonal shapes. Such extended area flange configurations may, as mentioned, be of assistance in providing grippable or manually graspable area to facilitate the donning operation involving the article.

Further, it is to be appreciated that the apertures in the flange element(s) of tubular articles of the present invention, may have any suitable aperture shape. For example, the flange element may have an opening which is round or circular in shape, or alternatively, the opening may be of square, oval, rectangular, or other non-circular and/or polygonal shape. The flange element opening may also be constituted as a slit, of linear or non-linear character, e.g., a serpentine or a sawtooth slit.

It will be recognized from the foregoing that the flange element(s) of the article of the present invention, in condom applications, provide an enhanced sealing structure, relative to prior art condoms. Specifically, when donned, the inner periphery of the flange element (bounding the central aperture of the flange element) bears compressively against the base of the penis, at the flange element through which the penis initially was inserted for application purposes, and a second flange element, when employed, includes an inner edge bounding the central aperture which on the installed condom bears compressively against the outer surface of the applied condom and radially inwardly compresses the underlying sheath wall against the penis. Accordingly, in such dual flange condom construction, a "double sealing" is achieved of the condom article against the penis, thereby enhancing the leak-tightness of the condom, and enhancing its contraceptive efficacy and disease-preventive character, as compared to condoms lacking such flange structure.

Accordingly, in condom applications, the articles of the present invention achieve a substantial advance in the prophylactic art, in substantially increasing the safety, reliability, and effectiveness of the condom article, as well as enhancing its ease of use by its amenability to bi-directional donning.

Referring now to FIG. 1, there is shown a perspective view of one preferred type of condom "blank" (precursor structure) according to the present invention. As illustrated, condom tubular main sheath blank 1 comprises two flat sheets of condom tubular main sheath blank material 2, in substantial registration wherein condom tubular main sheath blank 1 is match cut from both sheets of condom tubular main sheath blank material 2 simultaneously, and the sides 3 and rounded end 4 are continuously heat sealed, leaving unsealed the open end 5 of the condom tubular main sheath blank 1. The cutting and heat sealing may be a single simultaneous process or may be carried out sequentially. Preferably, it is a simultaneous process. While the particular process parameters and equipment are not critical and are well known in the art, the process described in U.S. Pat. No. 5,036,863 has been found to be useful, and the disclosure of such patent hereby is incorporated by reference in its entirety.

Figure 2:
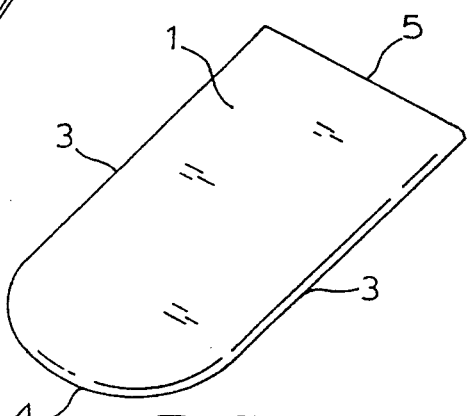
FIG. 2 is a perspective view of the finished tubular main sheath blank of FIG. 1.

FIG. 2 shows the completed cut and heat-sealed condom tubular main sheath blank 1 of FIG. 1, with the excess blank material removed.

Figure 3:
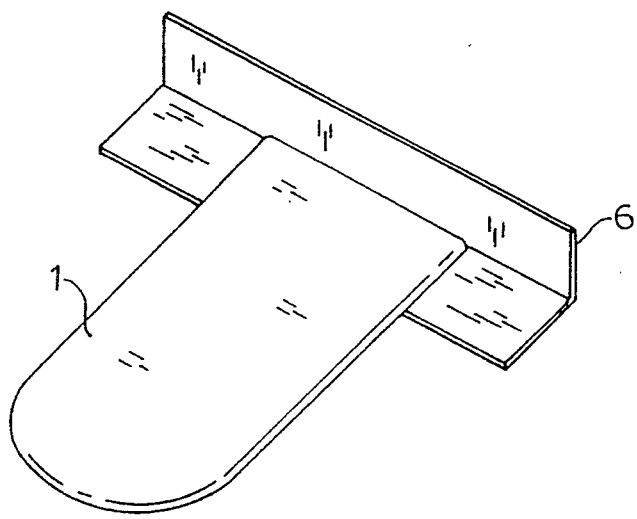
FIG. 3 is a perspective view of the finished tubular main sheath blank of FIG. 2 with a partially folded flange material over the open end of the condom tubular main sheath blank.

FIG. 3 shows the completed condom tubular main sheath blank of FIG. 2, with flange material 6 partially folded to enclose open end 5.

Figure 4:
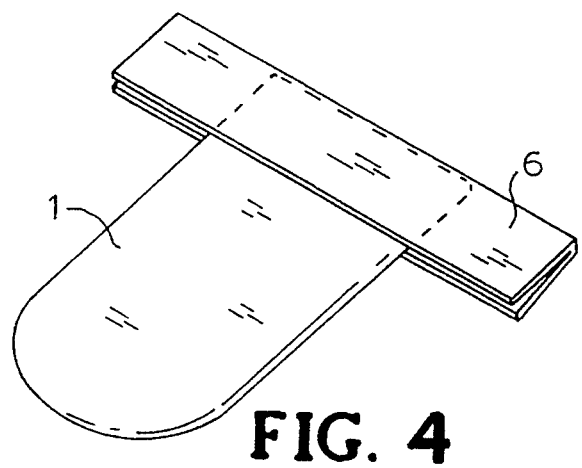
FIG. 4 is a perspective view of the finished tubular main sheath blank and the completely folded flange material ready for sealing and die cutting.

FIG. 4 shows a condom tubular main sheath blank 1 with open end 5 completely enclosed by fully-folded flange material 6.

Figure 5:
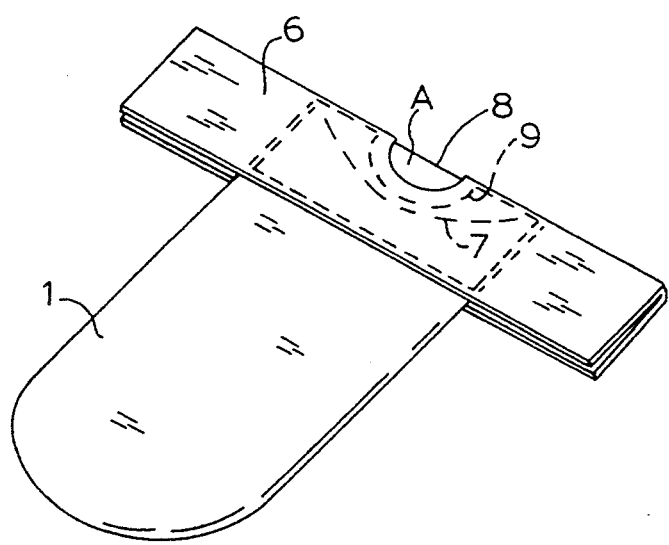
FIG. 5 is a perspective view of the tubular main sheath blank and flange material after the flange material has been sealed to the tubular main sheath blank and an aperture has been die cut through the flange material and the open end of the tubular main sheath blank; the figure also shows the "flag" member which is used in the sealing operation to prevent the tubular main sheath walls from being sealed to each other.

FIG. 5 shows the flange material 6 sealed by seal 7, e.g., a heat-sealed weld, to the condom tubular main sheath blank 1 and having a die-cut aperture 8 cut through the flange material 6 and the condom tubular main sheath blank 1 at open end 5 bounded by inner retention seal 9.

Although illustratively described with reference to securement of the first flange element to the sheath by heat-sealing, it will be recognized that the securement or affixation of the first and second flange elements and the sheath in the previously described manner may be effected in any suitable manner involving any securement means and/or methods which are usefully employed for the joining, attachment, securement, etc. of structural elements and which are usefully applicable to the flange elements and sheath portion in the articles of the present invention. In addition to heat-sealing, other illustrative potentially usefully employed securing approaches include ultrasonic bonding, melt-bonding, adhesive bonding, mechanical fasteners, interlocking arrangements, integral formation (wherein the sheath portion and flange elements are singly produced as a unitary product article), crimp-joining, or any other suitable method of bonding, joining, or connection.

The sheath member in FIG. 5 is shown as containing a "flag" element A, which serves as a barrier insert to prevent the respective sides of the sheath member from being bonded to one another when the heat sealing of the flange element 6 is heat-sealed to the sheath member. The "flag" element A is formed of a heat-resistant, non-bondable material of construction which is sufficiently flexible so that subsequent to bonding of the flange material to the sheath, the flag element can be pulled out of the interior of the heat-sealed structure through die-cut aperture 8.

Figure 6:
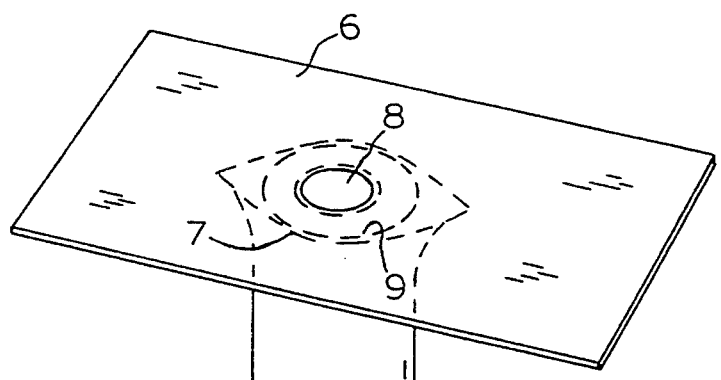
FIG. 6 is an isometric top view of FIG. 5 after the flange material has been unfolded, showing the opened tubular main sheath blank and flange material attached to one another at the open end of the tubular main sheath blank and having an aperture in the flange. Also shown is the inner seal of the tubular main sheath blank to the flange material.

FIG. 6 is a top isometric view of a preferred embodiment of the invention showing a condom tubular main sheath blank 1 sealed to flange material 6 at seal 7 and inner retention seal 9. A die cut aperture 8 through flange material 6 is provided by this construction, at the open proximal end of the condom tubular main sheath blank 1.

Figure 7:
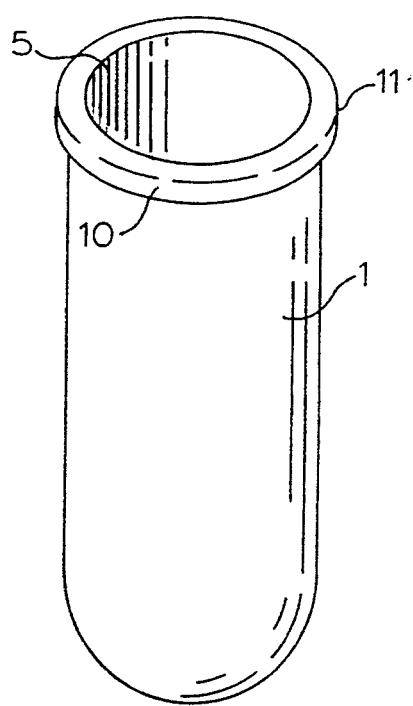
FIG. 7 is an isometric view of another embodiment of the tubular main sheath blank of the invention, as employed for subsequent open-tube welding.

In another preferred embodiment of the invention, FIG. 7 shows an isometric view of a condom tubular main sheath blank 1 having the proximal open end 5 of the sheath folded over to form an outer ring or skirt 10 forming a sealing surface 11.

Figure 8:
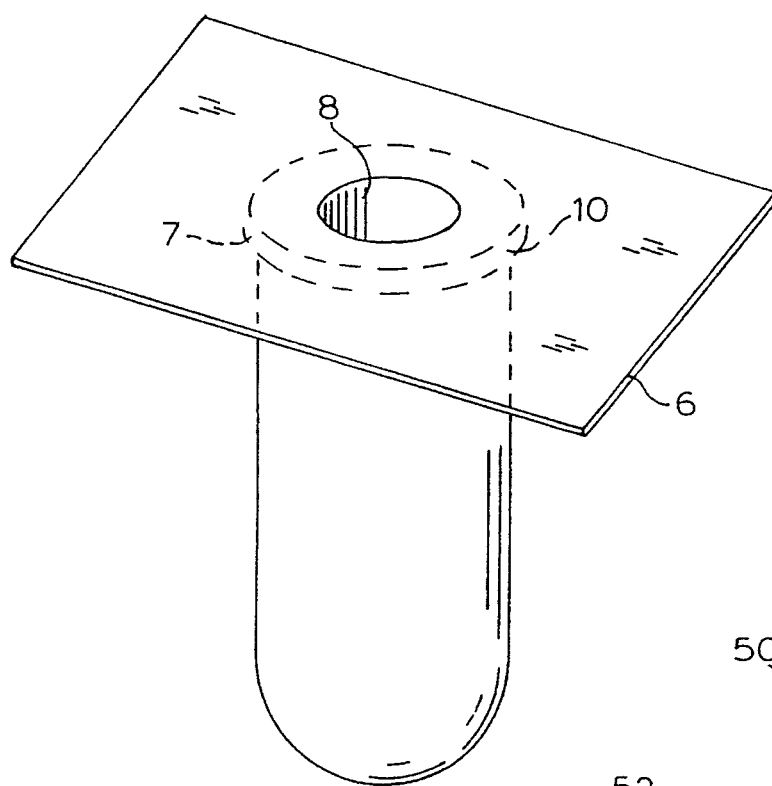
FIG. 8 is an isometric top view of the tubular main sheath blank of FIG. 7 with attached flange material having an aperture therein.

FIG. 8 shows the condom tubular main sheath blank 1 of FIG. 7 with flange material 6 attached at seal 7 and a die cut aperture 8 in the flange material 6 in substantial registration with the open end 5 (see FIG. 7) of the condom tubular main sheath blank 1.

Figure 9:
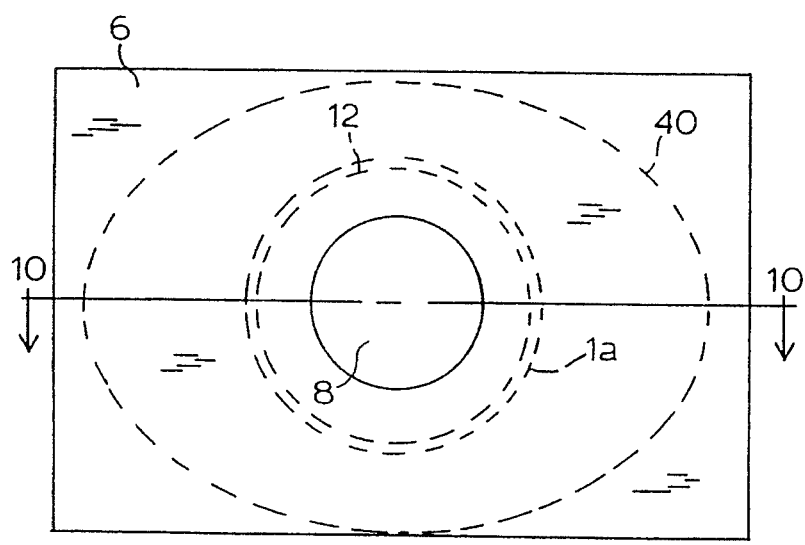
FIG. 9 is a top plan view of the embodiment of the invention shown in FIG. 8 showing the flange material with a die-cut aperture and the rolled and collapsed tubular main sheath blank beneath the flange material, with the collapsed tubular main sheath blank having a second flange/aperture element attached (far side).

FIG. 9 is a top plan view of the embodiment of the invention shown in FIG. 8 showing the flange material 6 with die cut aperture 8 and the condom tubular main sheath blank in a rolled form comprising toroidal roll 12 beneath the flange 6.

Figure 10:
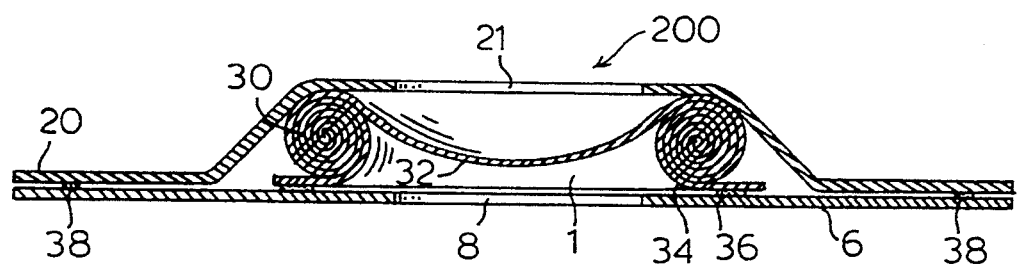
FIG. 10 is a side elevation view through section 10—10 of FIG. 9 with a second flange element attached around its periphery to the first flange element and enclosing the tubular sheath body.

FIG. 10 is a cross-section view in elevation, taken through section 10—10 of FIG. 9, showing the condom tubular main sheath blank 1 in rolled form comprising toroidal roll 30 circumscribing the distal end portion 32, and inscribing the proximal portion 34 of the sheath being sealed to flange material 6 at heat seal 36. The flange material 6 has the die cut aperture 8 at the condom tubular main sheath blank open end. By this arrangement, the flange material 6 provides a first flange element having an opening 8 which is in substantial registration with the distal end portion 32 of the main sheath. As shown, the condom tubular main sheath comprising toroidal roll 30 and distal end portion 32, as shown, is enclosed by a second sheet of flange material 20 sealed to flange material 6 around its periphery at heat seal 38. The second flange sheet 20 has a die-cut aperture 21 therein which is in substantial registration with die cut aperture 8 in the flange material 6, as well as in substantial registration with distal end portion 32 of the rolled main sheath.

Thus, referring to FIG. 10, there is shown a most preferred type of condom according to the present invention. As illustrated, condom 200 comprises a tubular main sheath having a closed distal end portion 32 and an open proximal end at proximal end portion 34 which is bonded to the first flange elements 6 at heat seal 36. The open proximal end of the condom secured to first flange element 6 has a die-cut aperture 8 therein with a diameter and cross-section that may be, and preferably are less than the diameter and cross-section of the main sheath of the condom. The condom tubular main sheath blank 1 is collapsed, as for example by doubling the distal closed end of the sheath back into the sheath and then rolling or folding the doubled tubular main sheath upon itself until it is fully collapsed (e.g., in rolled form) against first flange element 6. Thereafter, a second flange element 20 is placed over the fully-collapsed main sheath and the second element is sealed around its periphery to the periphery of the first flange element 6. The second flange has a cut aperture 21 therein, having a diameter and cross-section which may be and preferably are less than the diameter and cross-section of the main sheath itself. In this manner, the aperture 21 is substantially in registration with the distal end portion 32 of the main sheath blank as well as the aperture 8 of the first flange element. The sealed flange elements 6 and 20 are then suitably cut to form the desired final shape of the finished condom article flanges, as for example the oval shape shown in dotted line outline in FIG. 9. This cutting may be performed simultaneously with the sealing step or done separately afterward. The flange cutting or trimming step described for final shaping is an optional step, and the flange elements may be left in their original form, such as the rectangular form shown in FIG. 9. The final shape may be selected to facilitate manual gripping of the condom article for purposes of application of same to the penis of a wearer, and thus the size and shape of the respective first and second flange elements may be widely varied consistent with the ultimate form of the product which is selected.

Figure 11:
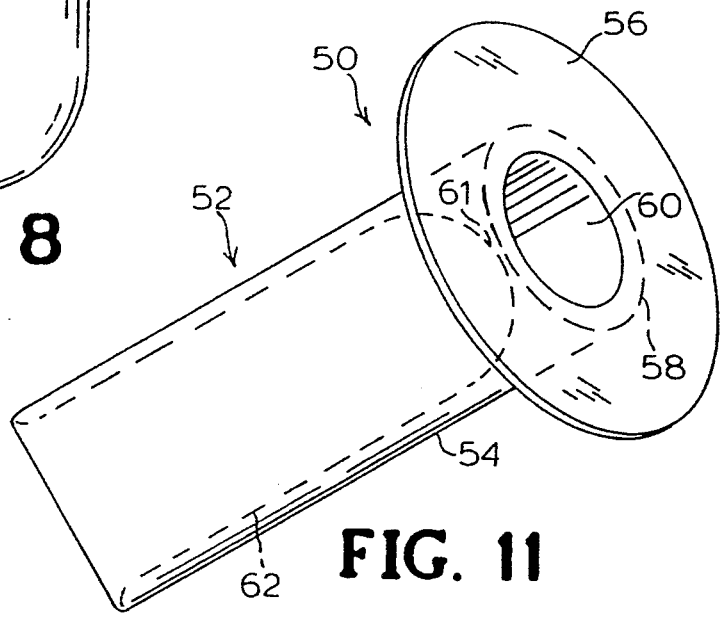
FIG. 11 is a perspective view of a single-flanged tubular article, wherein the distal segment of the sheath has been reentrantly inserted in the proximal segment of the sheath, so that the distal end is in proximity to, and registration with, the aperture in the flange element.

In respect of the foregoing discussion, it is to be appreciated that tubular articles of the present invention may be compacted for purposes of packaging, storage, etc., prior to their use, in any suitable manner. For example, the tubular article may be center-rolled as shown in FIG. 11, wherein the single flanged tubular article 50 comprises a main sheath portion 52 which is partially everted for subsequent rolling. Tubular article 50 includes a single flange element 56 to which sheath 52 is heat-sealed at seal 58, to provide a generally central flange element aperture 60, of smaller size than the proximal opening of the sheath (the proximal opening being generally associated with and bounded by heat seal 58). The distal part 62 of the sheath 52 has been everted to place same inside the proximal part 54 of the sheath.

In this everted configuration of the sheath 52, the distal end 61 of the sheath is in proximity to, and in general alignment with, aperture 60, and to accommodate the further compaction of the article, to form a center-compacted product article.

Figure 12:
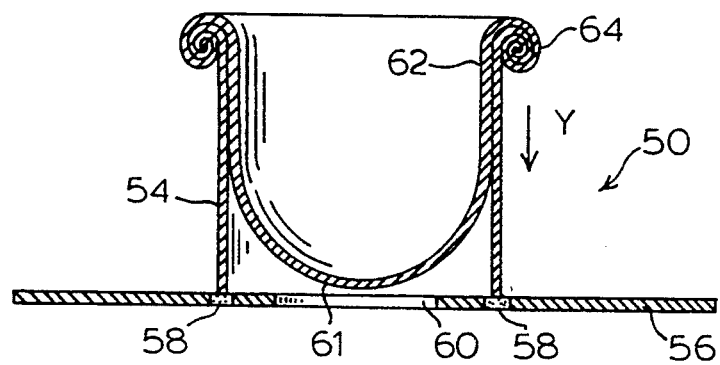
FIG. 12 is a sectional elevation view of an article of the type shown in FIG. 11, which has been partially rolled along the length of the re-entrantly folded sheath, toward the flange element.

FIG. 12 is a sectional elevation view of an everted sheath of an article of the type shown in FIG. 11, subsequent to partial rolling thereof toward the flange element 56. The numbered elements in FIG. 12 are numbered correspondingly with respect to the same elements in FIG. 11, for ease of reference. As shown, the partially everted sheath 50, comprising the distal part 62 re-entrantly disposed within proximal part 54, has been rolled toward the flange 56 to produce a toroidal roll 64, with the direction of rolling being indicated by arrow Y in FIG. 12.

Figure 13:
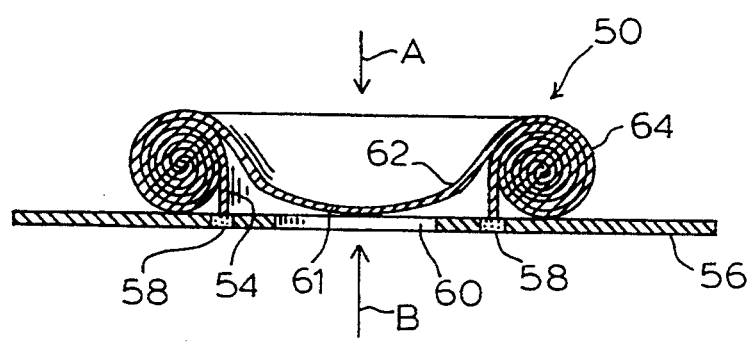
FIG. 13 is a sectional elevation view of the article of FIGS. 11 and 12, shown in fully compacted form, as a center-compacted product article.

FIG. 13 shows the article of FIG. 12 in a fully compacted form, as a center-rolled product article. As shown in FIG. 13, wherein all elements are numbered correspondingly to FIG. 12, the distal end 61 of the sheath is in proximity to, and aligned with, aperture 60 in flange 56, and the toroidal roll 64 is abuttingly disposed against the flange element 56. In such center-rolled configuration, the article is bi-directionally donnable in either of the directions indicated by arrows A and B. The body part or other structure to be sheathed, may be placed against either the interior surface of the distal end 61 followed by translation of the body part or structure to be sheathed, in the direction indicated by arrow A. Alternatively, the body member or structure to be sheathed may be disposed against the exterior surface of distal end 61 of the sheath through aperture 60, followed by translation of such body part or structure, in the direction indicated by arrow B.

Figure 14:
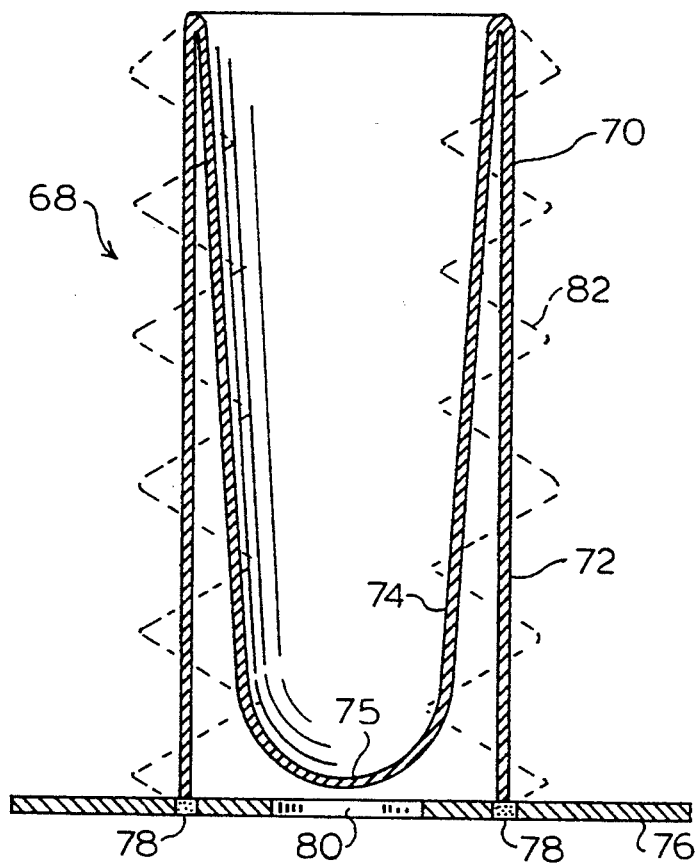
FIG. 14 is a sectional elevation view of an article comprising a partially everted sheath, ready for compaction to yield a center-compacted product article.

FIG. 14 is a sectional elevation view of a single flanged article 68 according to another embodiment of the present invention, wherein the sheath 70 has been partially everted so that a distal part 74 of the sheath has been re-entrantly disposed inside a proximal part 72 of the sheath. The article comprises flange element 76, which is joined to the sheath 70 at its proximal open end, by means of heat seals 78. In this everted configuration, the distal end 75 of the sheath is in proximity to, and generally aligned with, aperture 80 of flange element 76.

Figure 15:
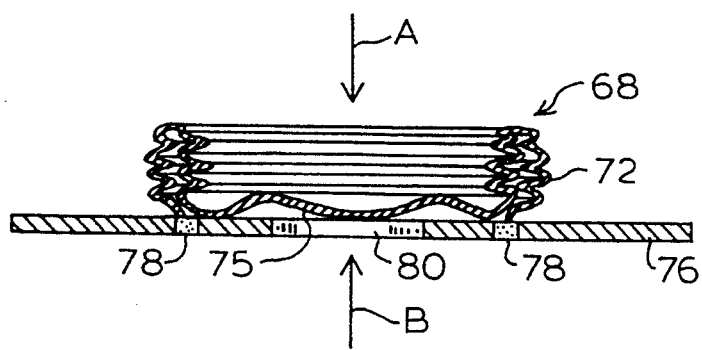
FIG. 15 shows the article of FIG. 14, in a center-compacted form.

The article comprising the partially everted sheath thus may be compacted by accordion-folding of same along the fold lines 82 shown in FIG. 14, to yield the correspondingly compacted article 68 shown in FIG. 15, wherein all elements are numbered correspondingly with respect to FIG. 14.

As shown in FIG. 15, the proximal end 75 of the sheath is abuttingly disposed against the flange element so that the tubular article can accommodate donning in either of the directions indicated by arrows A and B. Additionally, the shirred or compacted sheath configuration permits the center-compacted product article to be readily packaged for ultimate use.

In use, the article shown in FIG. 15 may be applied to the body part or other structure to be sheathed, with the body part or sheath in contact with the upper surface of distal end 75 of the sheath, with reference to the orientation shown in FIG. 15, followed by extension or translation of the entity to be sheathed in the direction indicated by arrow A. Alternatively, the entity to be sheathed may be disposed against the bottom surface of distal end 75 of the sheath, through aperture 80, followed by translation of the entity in the direction indicated by arrow B.

Referring again to the double-flanged condom article shown in FIG. 10, when the condom article shown in FIG. 10 is applied to the penis of a wearer, the penis may be inserted from either side of the condom article, through the aperture 8 in the first flange element 6, or alternatively through the aperture 21 in the second flange element 20, whereby the inserted penis then may be extended or directed into the main sheath of the condom, or, if the sheath is in a rolled form comprising a toroidal roll surrounding the distal end portion 32 as shown in FIG. 10, the penis may have the condom applied thereto by positioning the tip of the glans against the distal end portion 32 of the sheath followed by manual gripping of the periphery of the bonded flange elements 6 and 20 and manual drawing of the flanges toward the wearer, so that the sheath is unrolled onto the penis in a conventional manner, as regards the application of rolled condom devices.

Subsequent to installation of the condom article of FIG. 10 on the penis of a wearer, the bounding edges of the respective flange aperture openings bear compressively against the associated portion of the penis, with the outer portion of one of the flange elements bearing compressively directly against the circumference of the penis, and the edge of the opening in the other flange element bearing directly against the outer surface of the sheath and indirectly against the circumference of the penis thereunder, thereby providing retention and an additional barrier to the leakage of semen from the condom subsequent to ejaculation, as well as to disease-transmission between the coital partners.

By sandwiching a collapsed or center-rolled condom sheath between two layers of flange material the dual flange packet maintains its integrity until the donning motion has begun. By the nature of its design the preferred embodiment of the condom "pays out" the sheath of the condom as the dual flange structure is simultaneously drawn down the shaft of the penis. This construction thereby reduces air entrapment within the condom body during donning. It also substantially reduces drag associated with donning an unrolled condom, by eliminating the full unrolling/unfolding of the condom before donning. Thus, by having the condom sheath half-rolled or collapsed on itself and held between two flanges, the sheath does not unroll or otherwise outwardly extend until the donning motion begins. Further, this condom as a result of its dual flange packaging is significantly easier to hold and properly orient than previous condom designs. In this respect, the flange elements of the article of the invention provide an extended area structure for gripping and thus facilitate the manual handling and installation of the tubular article. Further, in contrast to condom devices of the prior art utilizing a pubic shield or other member attached at the proximal end of the condom, which in use may tend to separate at the junction between the condom sheath and the pubic shield, the tubular article of the present invention, utilizing multiple flange elements which are secured to one another provides increased structural integrity and strength relative to the pubic shield/condom articles of the prior art.

In prior practice all condoms, including slip-ons and roll-ons, have had to be situated correctly on the penis before successful donning could begin. In the case of roll-on condoms it is necessary to feel or visually inspect the condom in order to face the penis correctly. The multi-flange condom of the present invention by contrast, can readily be entered from either side, so that there is no difference in penetrating (donning) the condom from one side or the other. This is a distinct advantage over the prior art condoms in that incorrectly placing the prior art condom on a penis created the risk of transferring STDs and semen to a recipient coital party.

Another advantage of the present invention relates to lubrication, in that the lubricant is maintained predominantly on the condom thus hindering migration to the packaging material. In the illustrative embodiment of the invention described hereinabove with reference to FIG. 10 and related drawings, two flanges are sealed together around their perimeter to form a "packet" containing the condom body with the only openings being an aperture on either side. It may be desirable in some instances, by appropriate packaging or preferably with a light-tack adhesive, such as Poly-ox for example, to lightly seal the flange openings to the condom body tip so that the resultingly sealed packet can contain a specified amount of lubricant or "filler" material(s), with such materials being provided on both sides of the condom. The filler might be used to add thickness to the flange grips and thus further facilitate handling. The filler can also contain a medicant, such as for example, a spermicide, bactericide, anti-viral formulation, etc. The light tack may also aid in maintaining the integrity of the condom article.

An alternative means of totally enclosing the sheath member to form a packet involves the laying of material such as Poly-ox fully across both sides of the packet, instead of tacking the perimeter of the respective apertures to the distal tip portion of the sheath. With such construction, the outer film packaging layers could simply be peeled away or otherwise manually opened to extract the condom article of the invention, or alternatively the outer packaging layers could be perforated or weakened, (e.g., of reduced thickness) in order for the penis to break through such outer packaging layers, which could constitute additional flange elements of the overall structure.

As a further alternative, the flange elements, particularly in a multiple flanged configuration, could themselves be formed with perforated or weakened areas such that on installation the break-through of the penis would form the aperture openings in the respective flange elements, as opposed to prior die-cutting or other prior formation of such aperture openings.

It will be appreciated that the invention may be practiced in a wide variety of ways, as regards the packaging of the tubular article, and that considerations such as materials of construction, sterility considerations, and mass producibility may determine the specific form of the packaging of the article which is most advantageously employed in a specific embodiment of the present invention. Another advantage of the present invention is that the flange material and the sheath member can be formed of different materials. The preferred fabrication of the article of the invention also permits the sheath to be stress-softened, as more fully described in U.S. application Ser. No. 07/775,783 filed Oct. 11, 1991 in the names of Robert G. Wheeler and William D. Hawley, the disclosure of which hereby is incorporated herein by reference, with such stress-softening of the sheath being carried out prior to the sheath being secured to the flange element(s).

The use of two flanges in the article of the invention allows for the incorporation of surprisingly large apertures in the respective flanges. The tubular member (main sheath portion), while being donned, will always, by nature of the dual flange construction, be drawn through one of the two apertures by the body part being sheathed. Correspondingly, the body part will always be directed through and situated within two apertures. The film thickness of the sheath between the body part and the aperture, the retaining force exerted by the two separate flanges, and the relative position of the two apertures all allow for a suprisingly large diameter flange aperture. For example, when utilizing either ELASTOLLAN ® polyurethane or Deerfield KRATON ® blend polyurethane in a condom article according to the present invention, an aperture of up to 1¼ inch may be used. Previous single flange designs, as for example the flanged condom shown in FIG. 3 of U.S. Pat. No. 4,964,416, have employed aperture diameters in the range of ½ inch to ¾ inch. The maximum permissible diameter of the double flange apertures typically is affected by changes in film thickness, film type, surface treatment, and type and amount of lubricant, as may be readily ascertained by those skilled in the art without undue experimentation.

The flanges employed in articles according to the present invention may have any suitable shape, size, and thickness, consistent with the end use of the appertaining product articles. For example, the flange element may have a thickness which is greater than, less than, or substantially equal to the thickness of the main sheath of the article, depending on the desired end use of the article. In most applications, including condom usages, wherein the flange element is formed of a film material, the thickness of the flange element typically may be from about 0.1 to about 20 times the thickness of the sheath of the article, more preferably from about 0.5 to about 5 times the sheath thickness, and most preferably from about 0.75 to about 3 times such sheath thickness. It will be recognized that non-film materials of construction may be usefully employed for the flange, e.g., foam materials or fabric materials, of substantially greater thickness and flange/sheath thickness ratios than are characteristic of articles of the present invention comprising flange elements formed of film materials.

The flange element may, as previously discussed, have any suitable shape, consistent with the end use of the associated article of which it is a part. For example, the flange may be of square or rectangular shape, or alternatively it may be of a circular, oblong, or other shape, either polygonal in form or otherwise characterized by curvate or irregular peripheral edges.

Further, the flange element may be provided in a modified form to enhance the grippability of the flange structure, as for example with increased thickness edge portions which specifically are gripped by the hands of the user, or openings through which the fingers may be inserted and locked to apply the sheath to the body part or other structure to be sheathed.

Further, while the flange element has been described as preferably including an aperture formed or pressure-formable therein, of a size which is generally smaller than the proximal end opening of the sheath per se, it is within the purview of the invention to utilize aperture openings which are approximately the same size as the proximal sheath opening (the aperture opening in such instance being slightly smaller than the sheath proximal opening, in order to accommodate securement of the proximal end of the sheath to the flange element). It is, however, preferred to utilize an aperture opening of suitably smaller size than the proximal sheath opening, in order to achieve a positive sealing effect by the compressive bearing of the edge surface (bounding the aperture) against the sheathed entity, for purposes of leak-tightness, particularly in condom usage of articles of the present invention.

While not shown, it is contemplated that condom articles according to the present invention may comprise a sheath including a distal closed end reservoir for retention of ejaculate.

Condom articles in accordance with the present invention preferably are constructed by joining separate flange materials flange elements) to a pre-formed tubular main sheath. Earlier condom (viz., designs of the prior art) attempted to form a flanged condom by gusseting and heat-sealing a single piece of film material. Such method of prior art construction presented problems involving registration, machine tolerances, and film tension and integrity. The present invention represents a significant and unanticipated improvement in these areas. One major problem encountered by these earlier designs is an excessive amount of friction or drag while the condom is being donned. This is in part due to how the condom was formed and sealed in a lay flat condition. The dual flange article-forming machine described hereinafter overcomes such problem by joining a separate flange material to a pre-formed tubular main sheath such that the condom body is in an "open tube" configuration. This automatically allows the condom to repose in an open configuration. This subtle difference becomes very noticeable even while donning a loose, unrolled condom of the present invention, simply because the penis is not attempting to "part" the condom walls while entering. Combined with center-rolling, or accordion folds, the circular attachment of the sheath to the flange element in condom articles of the present invention facilitates a more effortless entry.

The dual-flange machine hereinafter illustratively described, by accommodating separate components of the condom, gains much needed control over the film material, and simplifies registration and aperture punching by permitting the majority of construction to be carried out in a compact, stop-motion work station. While the ensuing description herein is oriented toward use of reels of single width flange material, it is understood that corresponding apparatus can be adapted to work with full width film rolls.

The dual-flange machine hereinafter described, combines aperture cutting, flange-to-condom tubular main sheath blank attachment, stress-softening, rolling and perimeter cut/sealing of the finished product. Support welding and textural stamping may be achieved in this final operation since the flanges are laid flat during the forming process. In one form, the apparatus has as one of its major components a piston (plunger)/bladder device (other means than a bladder could be used in this device to similar benefit) that inverts the inflated, blow-softened tubular main sheath blank. A most preferred embodiment of the invention utilizes a center-roll which allows the condom to unroll effortlessly with a gentle force from either direction.

Figure 16:
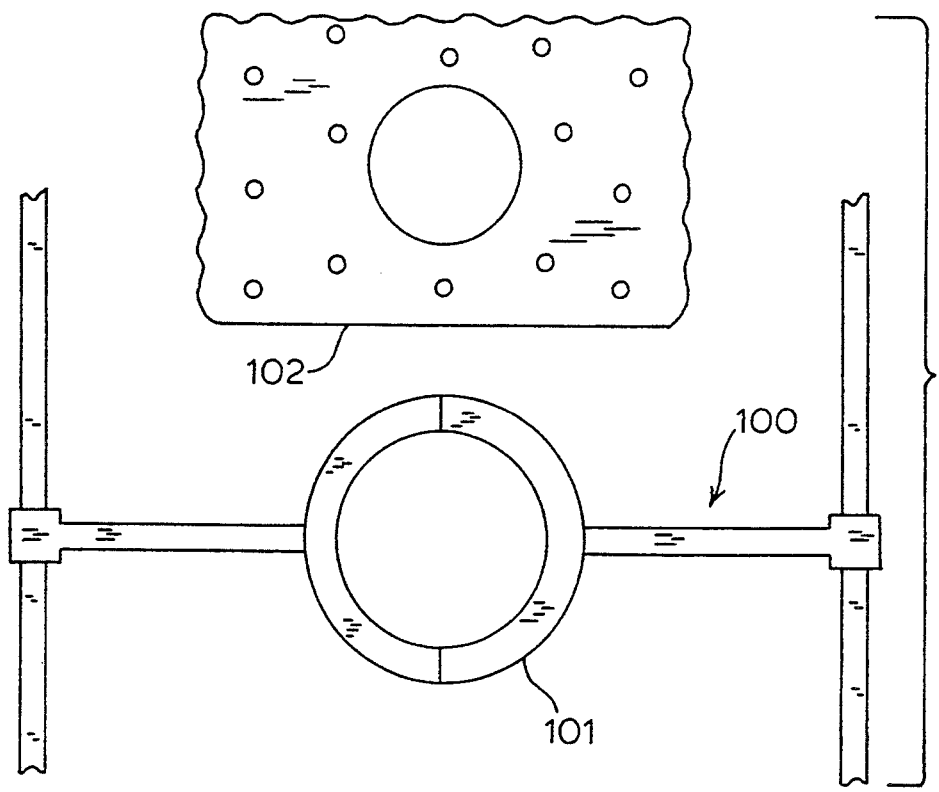
FIG. 16 is a partial top plan view of apparatus which may be used to seal the flange material and the tubular main sheath blank together.

Referring now to FIG. 16, there is shown a mounting ring assembly 100 comprising a two-part split ring 101 ready to receive a pre-cut tubular main sheath blank 1 while still in the cut/seal skeleton (not shown). The tubular main sheath blank 1 is placed over the mounting ring assembly 101 which in turn will move to a position over a vacuum bed 102. The vacuum bed in turn will hold the flange material 6 (not shown for clarity) in registration. The flange material 6, controlled by a guidance system (not shown for clarity), has die-cut aperture 8 punched prior to moving in line with the ring assembly 101.

Figure 17:
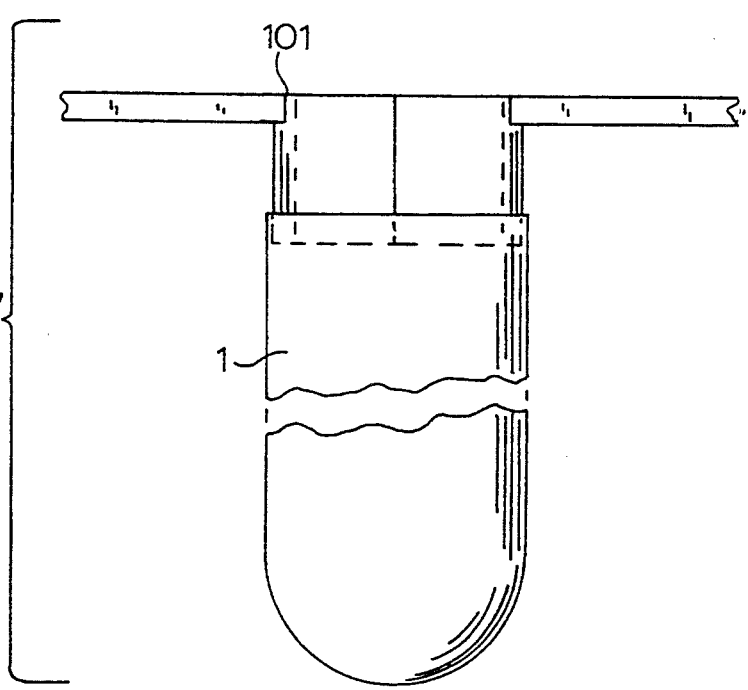
FIG. 17 is a partial side plan view of a tubular main sheath blank mounted on the ring assembly of the apparatus of FIG. 16.

FIG. 17 shows the tubular main sheath blank 1 mounted on the mounting ring assembly 101.

Figure 18:
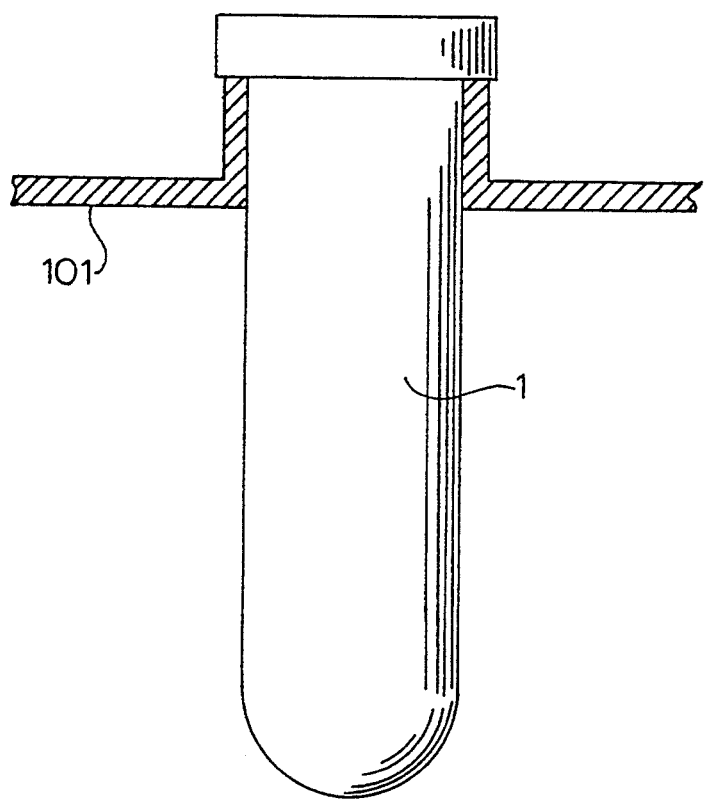
FIG. 18 is a partial side plan view of the tubular main sheath blank mounted on the ring assembly of the apparatus of FIG. 16 and having been blown therethrough, with the tubular main sheath blank inverted through the center of the mounting ring assembly.

FIG. 18 shows the condom tubular main sheath blank 1 inverted through the center of the mounting ring assembly 101. This inversion of the sheath blank on the mounting ring assembly 101 can be accomplished by any of several means commonly known to those proficient in the art of thin film assembly, e.g., by means of a continuous air stream (not shown for clarity) or by mechanical means.

Figure 19:
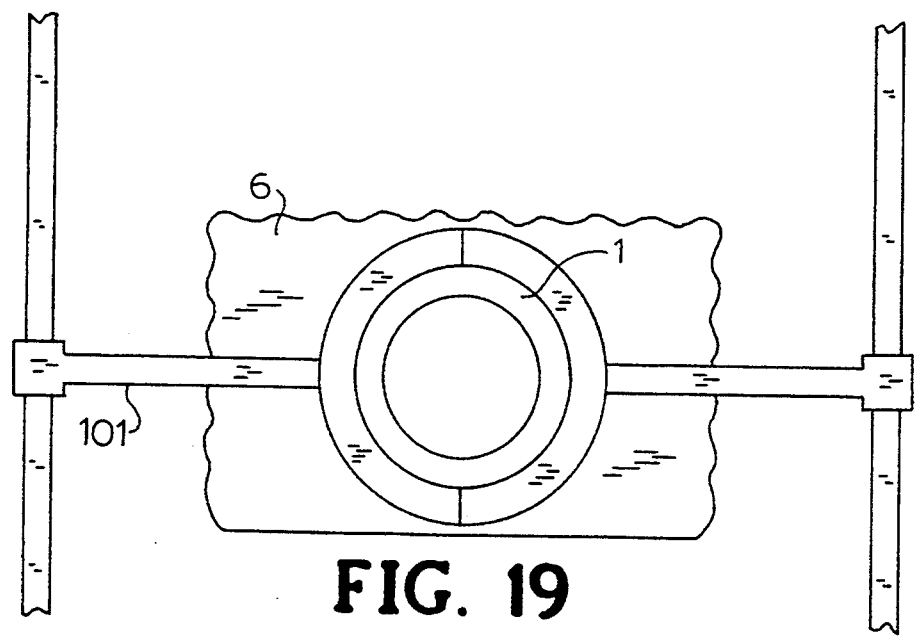
FIG. 19 is a partial top plan view of the ring assembly and blown tubular main sheath blank of FIG. 18 mounted over the vacuum bed having flange material placed thereon.
Figure 20:
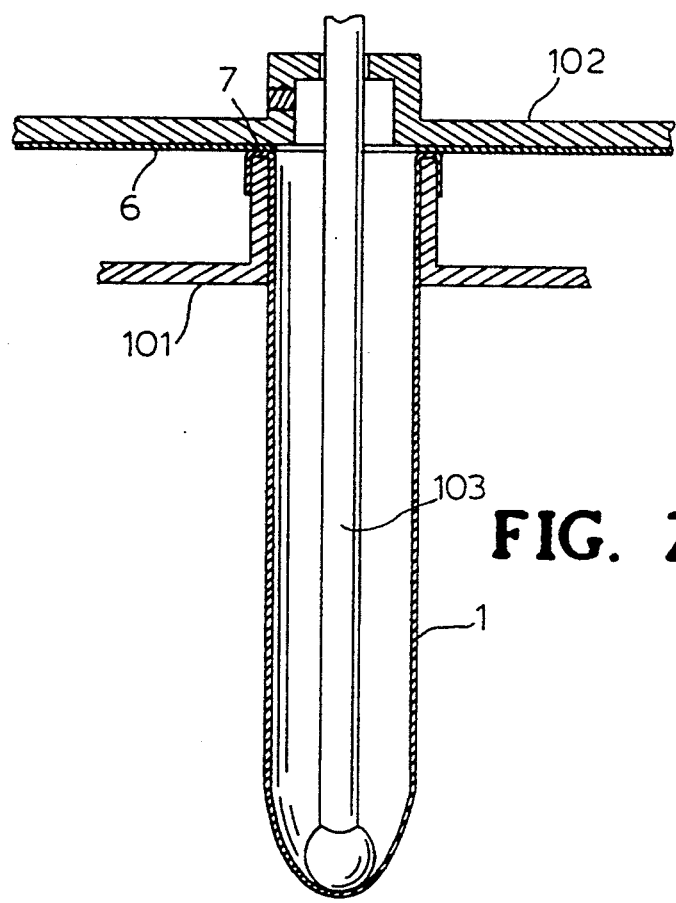
FIG. 20 is a partial side plan view of the tubular main sheath blank and the flange material sealed together on the apparatus of FIG. 16 where the tubular main sheath blank is partially prestretched via a mandril before the sealing takes place.

FIG. 19 shows the tubular main sheath blank 1 mounted on ring assembly 101 and the flange material die-cut aperture 8 in vertical registration. The tubular main sheath blank 1 on ring assembly 101 is moved into sealing contact with flange material 6 on vacuum bed 102. After sealing takes place, a pre-stretch mandril 103 travels through the ring assembly 101 and extends the condom tubular main sheath blank 1 a prescribed distance, as shown in FIG. 20.

Figure 21:
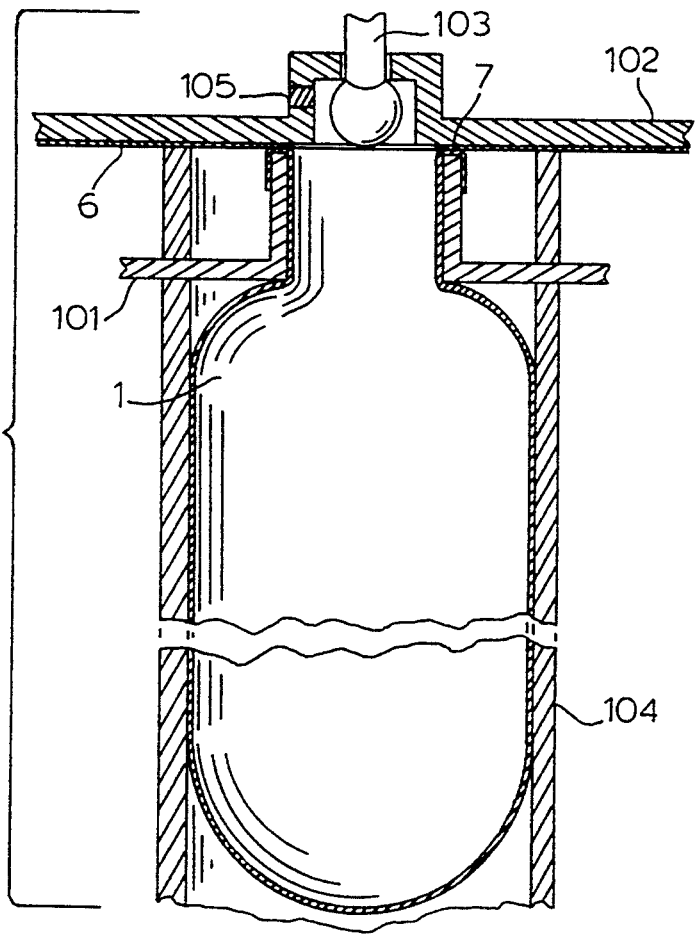
FIG. 21 is a partial side plan view of the tubular main sheath blank being fully stretched within a blow-stretch forming tube.

FIG. 21 shows the pre-stretch mandril 103 retracted; a blow-stretch tube 104 swings in line and centers on the sheath. Air from an air supply system (not shown) enters through passage 105 and inflates the tubular main sheath blank 1 to a prescribed volume.

Figure 22:
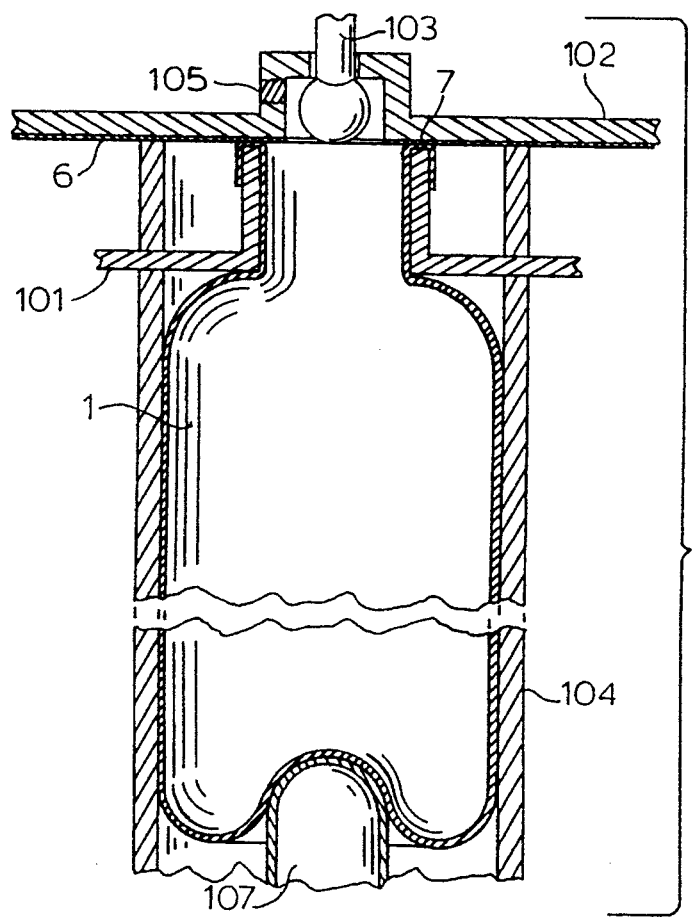
FIG. 22 is a partial side plan view of the fully stretched tubular main sheath blank beginning to be roll-collapsed to the flange material using the centering plunger assembly partially shown.

At full inflation, a centering plunger 107 with roll-off bladder is introduced at the distal closed end 4 of the tubular main sheath blank 1 to begin the inverting process, as shown in FIG. 22.

The centering plunger 107 may or may not have a vacuum face in contact with the distal end of the inflated tubular main sheath blank 1 to maintain centering. It is understood that air inside the condom tubular main sheath blank 1 must be displaced to allow for the increasing volume of the plunger 107 within the confines of the blow-stretch tube 104. To this end air is released through passage 105. As further shown in FIG. 22, there is an air-tight seal 106 between vacuum bed 102 and pre-stretch mandril 103.

Figure 23:
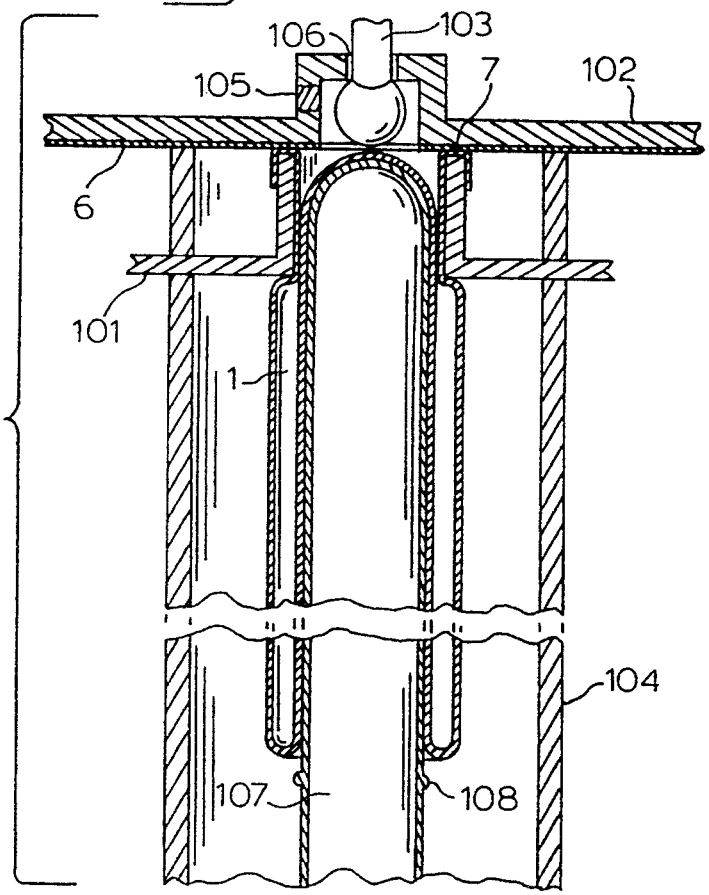
FIG. 23 is a partial side plan view of the fully stretched tubular main sheath blank doubled back upon itself after the centering plunger has fully extended.

FIG. 23 shows the tubular main sheath doubled back into itself with centering plunger 107 fully extended, the roll-off bladder associated with the centering plunger being uninflated and the optional roll-up band 108 being positioned to start rolling the tubular main sheath toward the flange 6.

Figure 24:
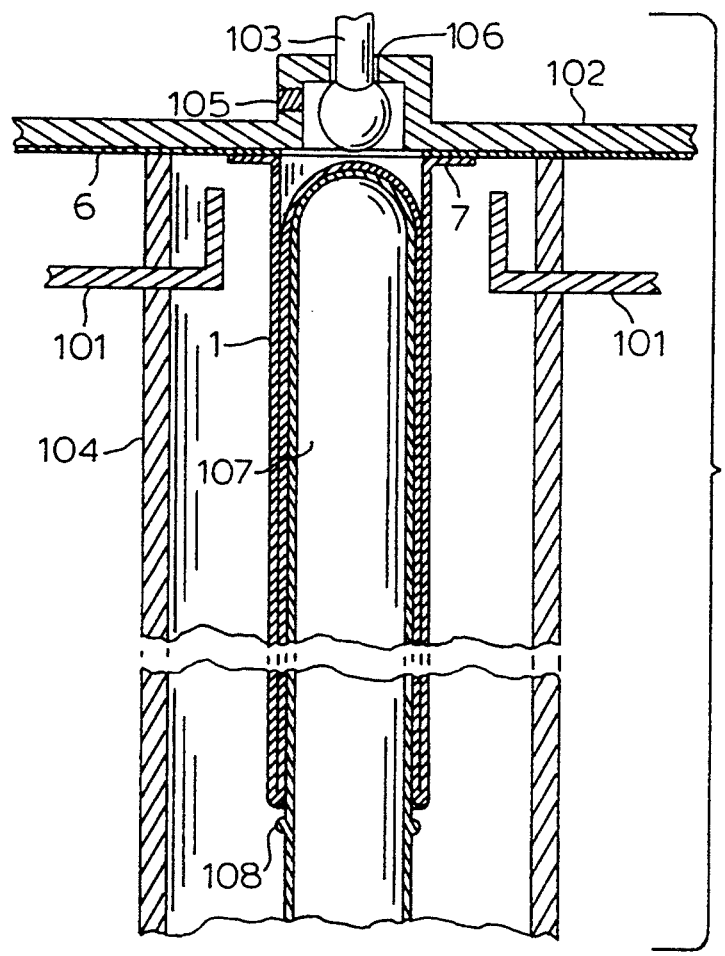
FIG. 24 is a partial side plan view of the tubular main sheath blank of FIG. 18 after the tubular main sheath blank has been collapsed against the centering plunger/mandril.

At this point there is little or no air pressure stretching the tubular main sheath. A vacuum may then be applied to the tubular main sheath through passage 105, thereby pulling the condom tubular main sheath tight against the centering plunger 107 and the flange material 6, as shown in FIG. 24.

Figure 25:
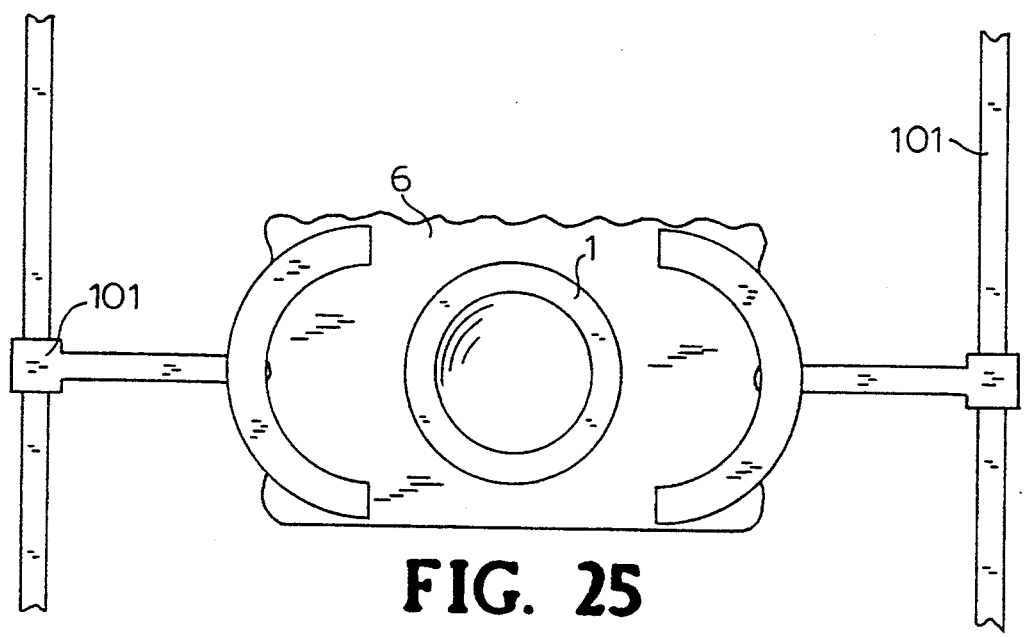
FIG. 25 is a top plan view of the mounting ring assembly in a raised and withdrawn position.
Figure 26:
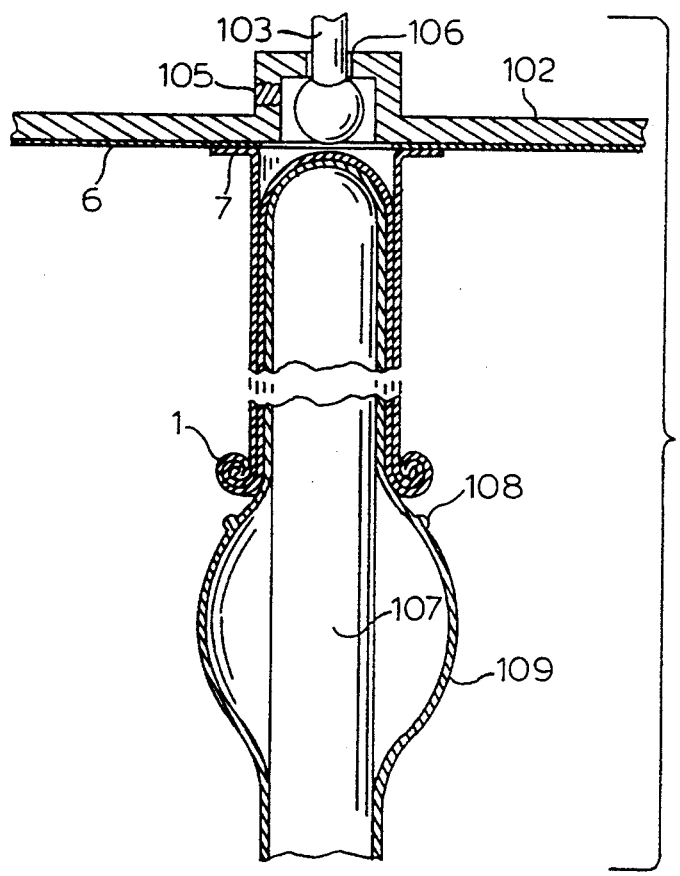
FIG. 26 is a partial side plan view of the tubular main sheath blank of FIG. 23 after the ring assembly has been removed and the roll-off mechanism has been partially activated to effect the initiation of rolling of the tubular main sheath blank.

FIG. 25 shows the ring assembly 101 raised and withdrawn from the condom. FIG. 26 shows the roll-off bladder 109 starting to inflate causing the (optional) roll initiator 108 to cause the tubular main sheath to quickly begin rolling toward the flange material 6.

Figure 27:
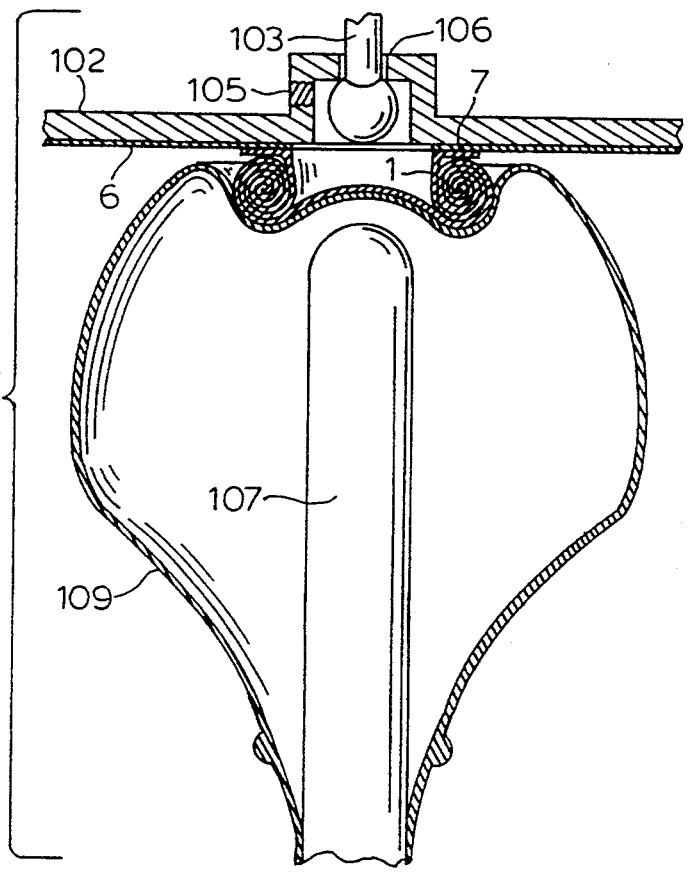
FIG. 27 is a partial side plan view of the roll-off mechanism completely activated and the tubular main sheath blank completely rolled into a collapsed condition.

When the roll-off bladder 109 is fully inflated (FIG. 27), the condom sheath is completely rolled up to a rolled state so that the roll reposes against the flange material 6. At this point the singly flanged condom, now rolled, is centered around the aperture and ready to receive the second flange 20 with die-cut aperture 21 (see FIG. 10).

The second flange material 20 is carried by a suitable conveyance system (not shown) which maintains the alignment and registration of the two die-cut apertures 8 and 21 with respect to one another. Finally, with each component layered and in vertical line, the perimeter of the flanges is cut and sealed forming an annular-shaped or other-shaped flange structure. Lubricant and/or other filler can be added at this point if desired. The circular weld which holds the shape of the rolled condom and any other texturing or sealing can take place in the same die strike. If desired, printing on the flanges can also be done at this point since registration is still held by the vacuum bed 102. The dual-flange condom then is part of a continuous strip of film ready for cutting and/or packaging.

Figure 28:
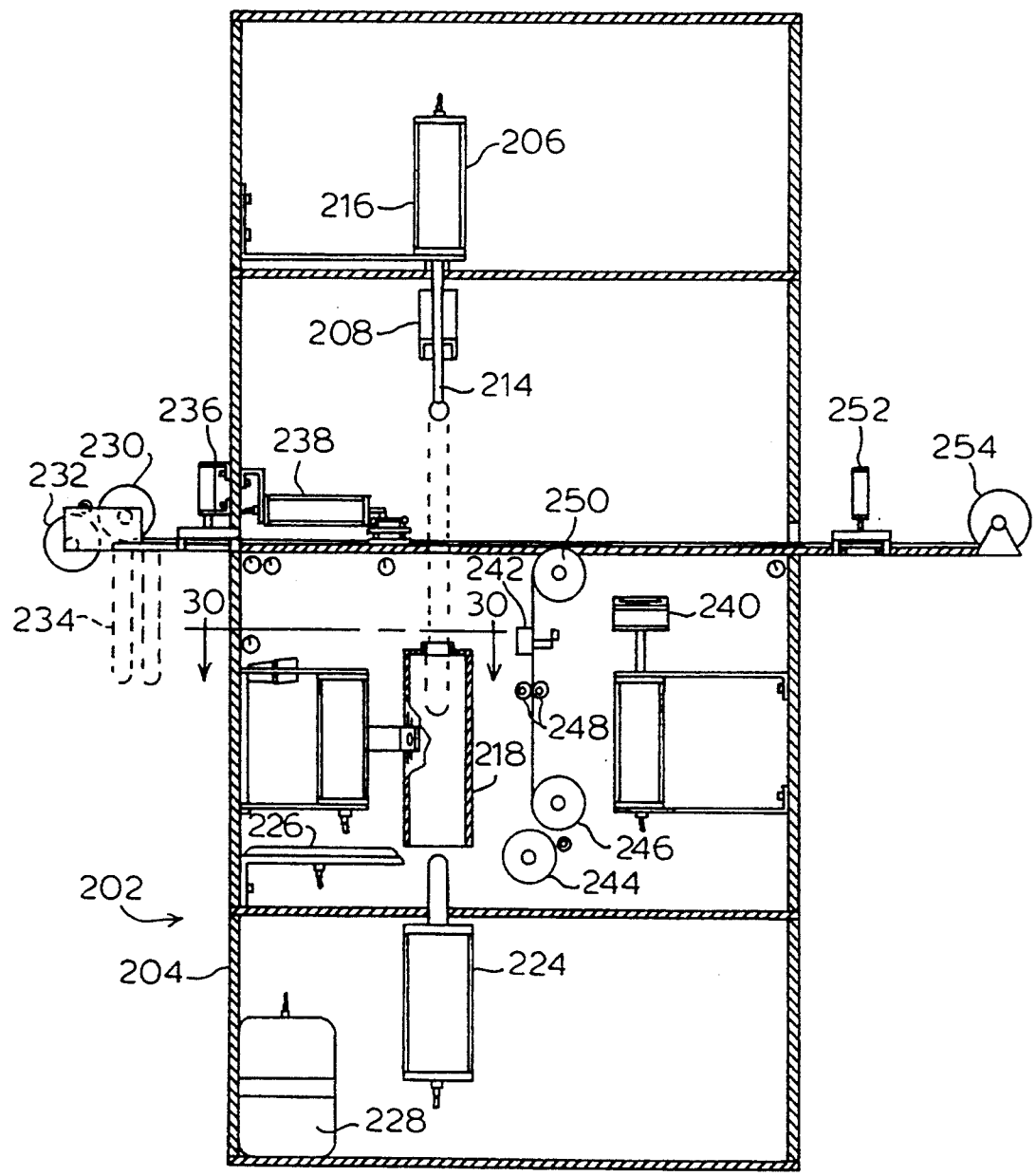
FIG. 28 is a front elevation view of an apparatus for forming a tubular article according to one embodiment of the invention.
Figure 29:
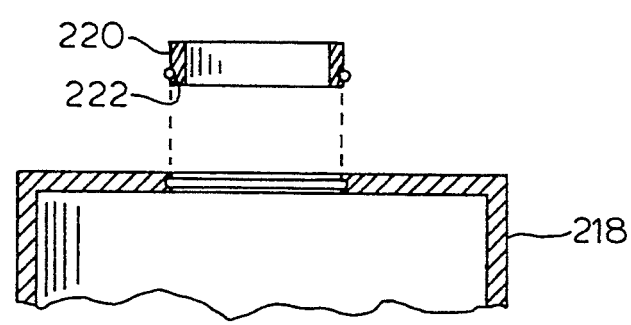
FIG. 29 is a sectional elevation view of the upper portion of the blow-stretch tube employed in the FIG. 30 apparatus, together with the sealing ring/O-ring elements associated therewith.
Figure 30:
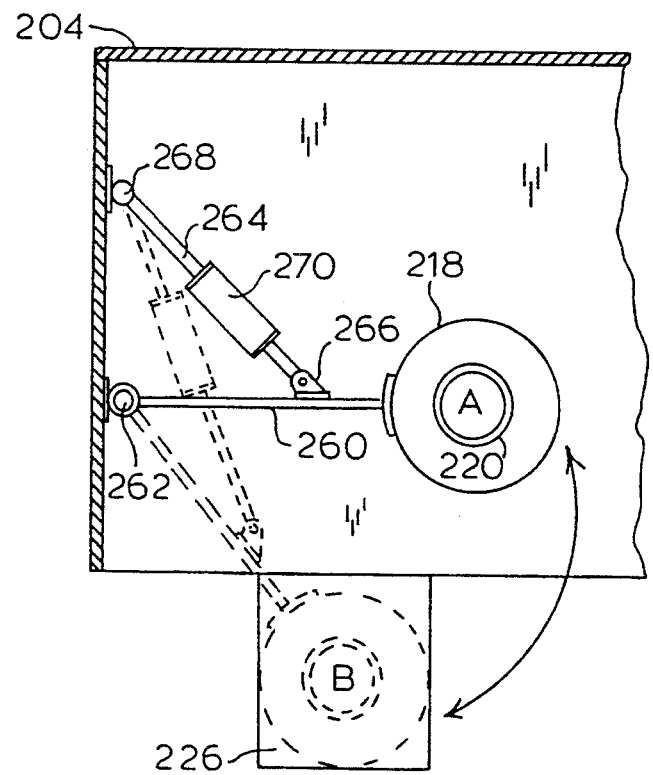
FIG. 30 is a sectional plan view of a portion of the FIG. 28 apparatus, taken along line 30—30 of FIG. 28, showing a portion of the apparatus including the blow-stretch tube and sealing ring, as well as the vacuum plate.

FIGS. 28–30 show various views of a condom heat-sealing and rolling machine for commercial manufacture of condom articles of the present invention, in mass quantity. The operation of such apparatus is more specifically described with respect to FIGS. 31–39, which depict relevant portions of the apparatus in steps 1–9 of a condom fabrication process associated with the machine of FIGS. 28–30.

Referring now to FIG. 28, the heat-sealing and rolling machine 202 comprises an outer frame or housing 204 of generally rectangular shape, within which various components of the overall system are mounted for operation. Within the upper portion of the housing is mounted a pre-stretch mandril and cylinder with shut-off tube 206, below which is a shut-off heat seal cylinder assembly 208, which comprises a heat seal element and a shut-off cylinder. The pre-stretch mandril 214 is shown protruding downwardly from the cylinder 216 of the mandril and cylinder with shut-off tube assembly 206.

Coaxially aligned with the pre-stretch mandril and cylinder assembly is a blow-stretch tube 218, which is shown in greater detail in FIG. 29 as comprising a removable sealing ring 220 and groove 222 associated therewith.

Beneath the blow-stretch tube and in coaxial alignment therewith is an inverting cylinder and mandril assembly 224. A vacuum plate 226 and vacuum tank 228 effects condom reversal. A supply roll 230 and peel-off roll 232 are employed to deliver flange material to the system, with suitable accumulator bars (not shown) providing overfeed material 234 to insure smooth and substained operation of the apparatus.

The FIG. 28 apparatus includes a punching cylinder and die unit 236.

The apparatus also includes a bottom heat seal cylinder 240, and a hole punch unit 242 for bottom flange stock supplied by supply roller 244 and peel-off roll 246. The system also includes a pair of oppositely rotating idle rollers 248 which are gear fed (by drive means not shown), and roll 250.

On the right-hand side of housing 204 is a knock-out die and cylinder unit 252 and a take-up roller 254 for the product articles.

FIG. 30 is a top plan view, in section taken along line 30—30 of FIG. 28, showing the internal structure of the apparatus mounted in housing 204. As shown, the blow-stretch tube 218 and removable sealing ring base 220 are mounted on an arm 260 for pivoting about hinge member 262 between the position shown as "A" in FIG. 30 to the position "B" in the same drawing. To facilitate such movement, the arm 260 has attached thereto a second arm 264 which joined at one end by connecting structure 266 to arm 260 and at its opposite end is joined by hinge member 268 to the wall of frame 204, being provided with a piston extension unit 270, by means of which the swing movement of the blow-stretch tube between positions "A" and "B" is achieved. At position "B", the blow-stretch tube is disposed over the vacuum plate 226.

The operation of the apparatus of FIGS. 28–30 will now be described with reference to FIGS. 31–39 hereof.

In Step 1 of the condom-forming process (FIG. 31), a sheath member is placed on the sealing ring associated with the blow-stretch tube 218. The blow-stretch tube then is rotated over the lower vacuum plate 226 (see FIG. 30; vacuum plate not shown in FIG. 31 for clarity), and the sheath 274 is reversed by vacuum into the blow stretch tube. The shut-off tube then seals the sheath against the pre-punched roll stock 230.

Figure 32:
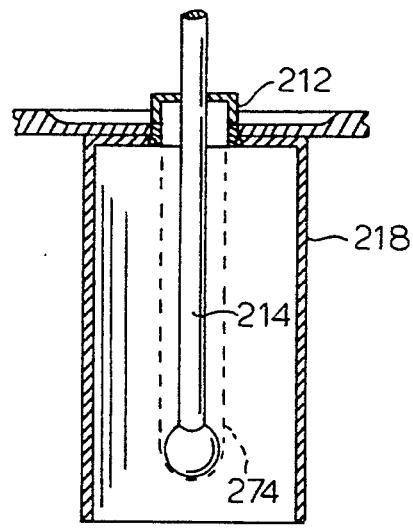
FIG. 32 is a view of the FIG. 31 apparatus, in a second step of a process carried out with such apparatus.
Figure 33:
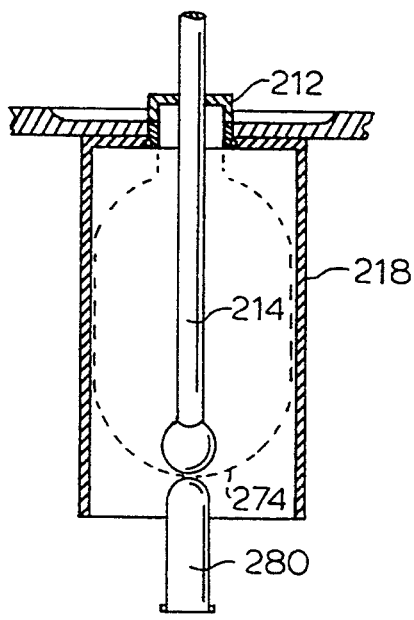
FIG. 33 shows the FIG. 31 apparatus, together with the inverting mandril, in a third step of the process carried out with such apparatus.

In Step 2, shown in FIG. 32, the pre-stretch mandril 214 stretches the sheath 274 to a predetermined length.

In Step 3, the sheath 274 is inflated to a predetermined pressure and size within the blow-stretch tube 218. (see FIG. 33).

Figure 34:
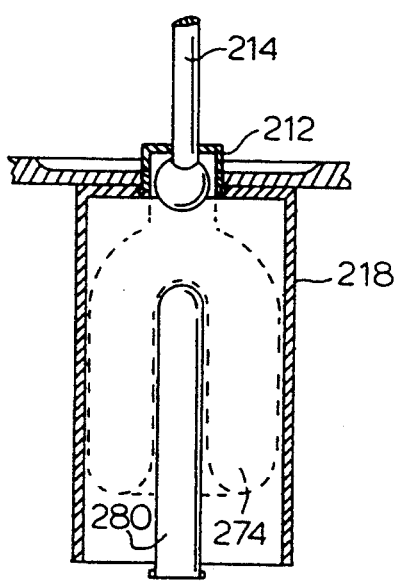
FIG. 34 shows the FIG. 31 apparatus, in a fourth step of the process carried out with such apparatus.

In Step 4, shown in FIG. 34, the inverting mandril 280 folds the sheath into itself while the sheath is being deflated by pressure bleed off through the upper portion of the blow-stretch tube (specific deflation means not shown).

Figure 35:
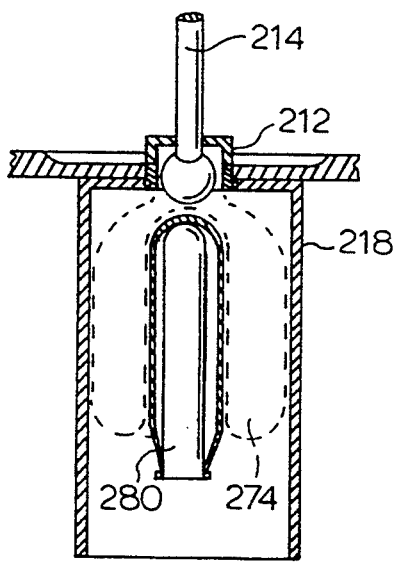
FIG. 35 shows the FIG. 31 apparatus, in a fifth step of the process carried out with such apparatus.

In Step 5, shown in FIG. 35, the inverting mandril is activated, rolling the sheath to the top of the blow-stretch tube 218.

Figure 36:
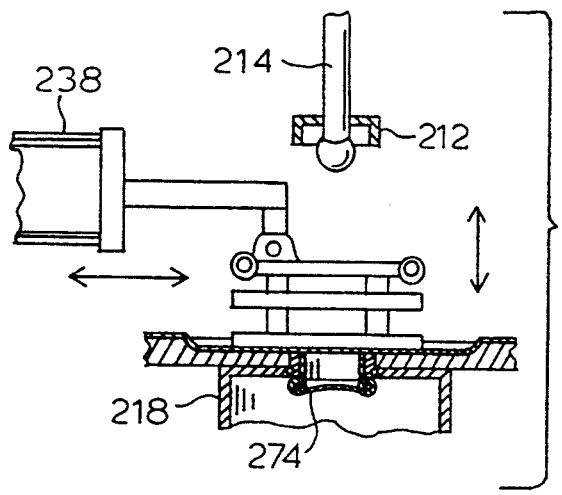
FIG. 36 shows the FIG. 31 apparatus, in a sixth step of the process carried out with such apparatus.
Figure 37:
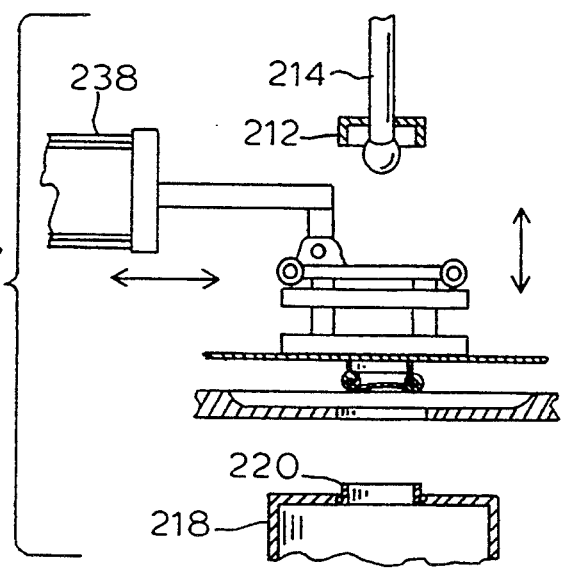
FIG. 37 shows the FIG. 31 apparatus with the associated vacuum plate assembly, in a seventh step of the process, carried out with such apparatus carried out with such apparatus.
Figure 38:
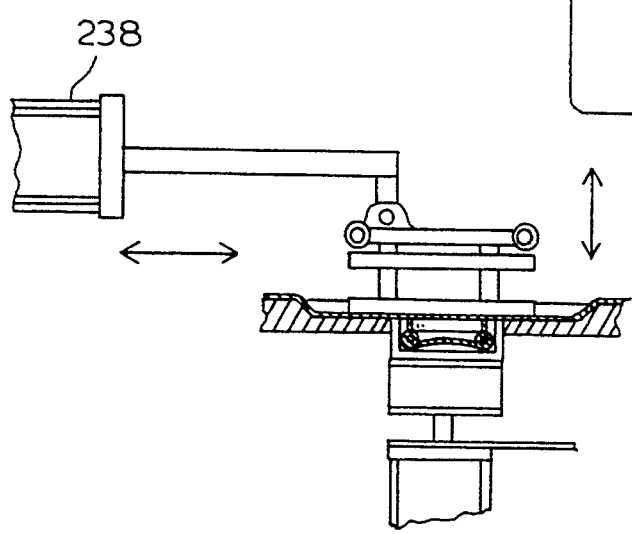
FIG. 38 shows the FIG. 37 apparatus, in an eighth step of the process carried out with apparatus.

In Step 6, shown in FIG. 36, the rolled sheath 274 is shown at the top of the blow-stretch tube, as the shut-off tube 282 is raised and the blow-stretch tube 218 is lowered.

In Step 7 (see FIG. 37), the singly-flanged condom is moved by a magnetic belt to the second sealing position.

In Step 8 (see FIG. 38), the resulting article is fed through the frame through an appropriately positioned opening.

Figure 39:
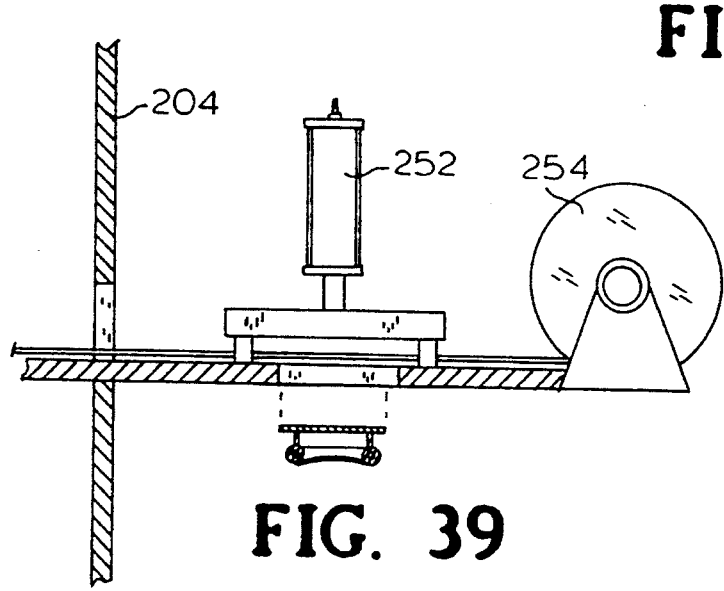
FIG. 39 shows the second punching station of the FIG. 28 apparatus, in a ninth step of the process carried with such apparatus.
Figure 31:
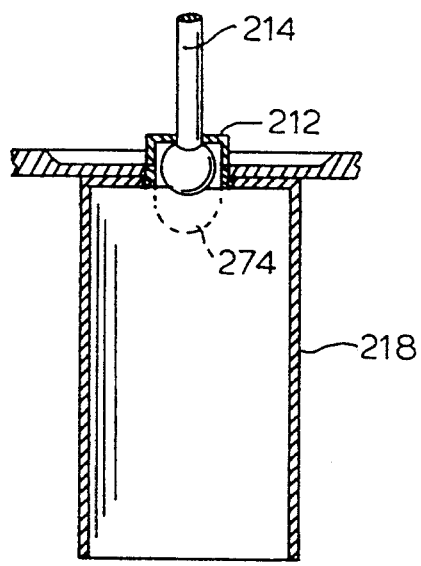
FIG. 31 is a partial sectional elevation view of a portion of the blow-stretch tube and spring/shut-off cylinder assembly, and mandril, illustrating a first step of a sheathing article-forming process according to one embodiment of the present invention.

In Step 9, shown in FIG. 39, the condom article advances to a second punching station where the condom article can be punched clear or perforated for subsequent removal.

The apparatus of FIGS. 28–30, the operation of which has been illustrated with respect to FIGS. 31–39, is usefully employed in the mass production of articles of the present invention, such as condoms, from suitable materials of construction, such as polyurethane materials. The apparatus illustratively shown in FIGS. 28–39 may also be integrated with other machine operations and equipment, such as the stress-softening and leak-testing apparatus described in prior copending application Ser. No. 07/775,783 filed Oct. 11, 1991, the disclosure of which hereby is incorporated herein by reference in its entirety.

While the invention has been described with reference, to specific embodiments and features, it will be appreciated that numerous modifications, variations, and embodiments of the invention are possible, and all such apparent variations, modifications, and embodiments are therefore to be regarded as being within the spirit and scope of the invention.

What is claimed is:

1. A bidirectionally donnable unitary article for sheathing a member, comprising:
   (i) a main sheath portion having an elongate form when fully extended, with a closed distal end, and an open proximal end,
   (ii) a first flange element integrally and permanently secured to the open proximal end of the main sheath and having an aperture formed or pressure-formable therein, in substantial registration with the proximal open end of the sheath, said first flange aperture having a diameter smaller than the diameter of the main sheath portion, and
   (iii) a second flange element integrally, directly and permanently secured at its outer peripheral portion to the first flange element, the second flange element having an aperture formed or pressure-formable therein, in substantial registration with the aperture of the first flange element, said second flange aperture having a diameter smaller than the diameter of the main sheath portion and wherein the main sheath is compactible to a compacted form reposable between the first and second flange element, with said first flange element aperture and said second flange element aperture diameter being sized to compressively bear against the outer circumference of the member when sheathed in the article wherein said open end of said sheath is encased between said apertures of said first and said second flange members.

2. An article according to claim 1, wherein the sheath is formed of a flexible and/or elastic material.

3. An article according to claim 1, wherein the first and second flange elements are formed of flexible and elastic material.

4. An article according to claim 1, wherein the first flange element is secured to the sheath and to the second flange element by heat seals.

5. An article according to claim 1, wherein the first and second flange elements have apertures formed therein.

6. An article according to claim 1, wherein the sheath is formed of a thermoplastic elastomeric material.

7. An article according to claim 6, wherein the thermoplastic elastomeric material is selected from the group consisting of:
   polyurethanes; polyether block amides; styrene-rubber-styrene block copolymers; polyesters; olefinic homopolymers and copolymers; and copolymers, composites, and alloys thereof.

8. An article according to claim 1, wherein the sheath is formed of a polyurethane thermoplastic elastomeric material.

9. An article according to claim 1, wherein the article is a condom consistently essentially of the sheath, first flange element and second flange element, and wherein the sheath is not associated with or secured to any garment structure.

10. An article according to claim 1, wherein the sheath has a thickness of from about 0.01 to about 0.10 millimeter.

11. An article according to claim 1, wherein the sheath has a thickness of from about 0.02 to about 0.05 millimeter.

12. An article according to claim 1, wherein the sheath has a diameter on the order of about 2 inches, and the aperture diameter of apertures in the flange elements is in the range of from about 0.5 to about 1.25 inches.

13. An article according to claim 1, wherein a filler is disposed between the first and second flange elements.

14. An article according to claim 13, wherein the filler comprises a material selected from the group consisting of: lubricants; medicaments; contraceptive materials; and mixtures thereof.

15. An article according to claim 1, wherein the first and second flange elements have apertures therein, and the article is disposed in a package.

16. An article according to claim 1, comprising additional flange elements overlying the first and second flange elements, such additional flange elements being manually removable from the first and second flange elements.

17. An article according to claim 1, wherein the sheath is center-compacted and disposed between the first and second flange elements.

18. An article according to claim 17, wherein the center-compacted configuration is a center-rolled configuration.

19. An article according to claim 1, wherein the article comprises a material of construction selected from the group consisting of: woven web materials, nonwoven web materials, thermoplastic film materials, natural rubber materials, synthetic rubber materials, and combinations, composites, and alloys thereof.

20. An article according to claim 1, wherein the main sheath portion is of cylindrical tubular form.

21. An article according to claim 1, wherein the main sheath portion is of a baggy configuration.

22. A bidirectionally donnable unitary condom article comprising:
a generally tubular main sheath portion, closed at a distal end thereof, and open at a proximal end thereof, including elongate panels continuously perimetrally heat-sealed to one another along side and distal margins thereof to form an interior volume of the sheath bounded by the panels, where the panels are formed of a flexible and/or elastic material;
a first flange element formed of a flexible and elastic material, and having an aperture therein, said first flange element being integrally and permanently secured to the main sheath portion such that the aperture of the flange element is in substantial alignment with the main sheath portion proximal open end, and wherein the first flange element aperture has a diameter smaller than the diameter of the main sheath portion: and
a second flange filament formed of flexible and elastic material and having an aperture therein with a diameter smaller than the diameter of the main sheath portion, said second flange element being integrally, directly and permanently secured to the first flange element around their respective outer peripheries to form an interior volume between facing surfaces of the first and second flange elements accommodating retention of the main sheath portion therein, in a compacted form, with said first flange element aperture diameter and said second flange element aperture diameter being sized to compressively bear against the outer circumference of a human penis when sheathed in the condom article wherein said open end of said sheath is encased between said apertures of said first and said second flange members.

23. A condom article according to claim 22, wherein the main sheath portion is rolled into a roll state comprising a toroidal roll circumscribing a distal end portion of the sheath, and the rolled sheath is disposed in the interior volume between the first and second flange elements, with the distal end portion of the sheath in substantial alignment with the apertures in the first and second flange elements.

24. An article according to claim 22, wherein the sheath is disposed in the interior volume between the first and second flange elements in a center-compacted configuration.

25. An article according to claim 24, wherein the center-compacted configuration is a center-rolled configuration.

26. A bidirectionally donnable unitary article for sheathing a member, comprising:
(i) a main sheath having an elongate form when fully extended, with a closed distal end and an open proximal end, and
(ii) a flange element integrally, directly and permanently secured to the open proximal end of the main sheath and having an aperture formed or pressure-formable therein, in substantial registration with the proximal open end of the sheath, and said flange element aperture having a diameter smaller than the diameter of the main sheath, a second flange element integrally, directly, and permanently secured at its outer peripheral portion to the first flange element, the second flange element having an aperture formed or pressure-formable therein, in substantial registration with the aperture of the first flange element, said second flange aperture having a diameter smaller than the diameter of the main sheath portion and wherein the main sheath is compactible to a compacted form reposable between the first and second flange element, wherein said open end of said sheath is encased between said aperture of said first and said second flange members,
wherein the main sheath is in a center-compacted configuration against the flange element, with the distal end of the center-compacted main sheath in general registration with the aperture of the flange element, and
wherein said flange element aperture diameter is sized to compressively bear outer circumference of the member when sheathed in the article.

27. An article according to claim 26, wherein the main sheath is of a baggy configuration.

28. An article according to claim 26, wherein the main sheath is of cylindrical tubular form.

29. An article according to claim 26, wherein the center-compacted configuration comprises a center-rolled configuration.

30. A method of making a bidirectionally donnable unitary article for sheathing a member, said sheathing article including a generally tubular main sheath portion including an open proximal end and a closed distal end, comprising:
integrally, directly and permanently securing a flange element of a flexible and elastic material to the open proximal end of the main sheath portion;
providing a formed or pressure-formable aperture in the flange element having a diameter smaller than the diameter of the main sheath portion; and
compacting the sheath into a center-compacted form with the distal end of the sheath in substantial registration with the formed or pressure-formable aperture positioning a second flange element of a flexible and elastic material over the first flange element having the sheath compacted thereagainst, and integrally, directly, and permanently securing the second flange element to the first flange element around their respective outer peripheries, providing a formed or pressure-formable aperture in the second flange element in substantial alignment with the formed or pressure-formable aperture in the first flange element, said second flange element aperture having a diameter smaller than the diameter of the main sheath portion, wherein the flange element aperture diameter is sized to compressively bear against the outer circumference of the member when sheathed in the sheathing article, wherein said open end of said sheath is encased between said aperture of said first and said second flange members.

31. A method of making a bidirectionally donnable unitary sheathing article including a generally tubular main sheath portion including an open proximal end and a closed distal end, comprising:

integrally and permanently securing a first flange element of a flexible and elastic material to the open proximal end of the main sheath portion;

providing a formed of pressure-formable aperture in the first flange element, said aperture having a diameter smaller than the diameter of the main sheath portion;

compacting the sheath into a compacted form;

positioning a second flange element of a flexible and elastic material over the first flange element having the sheath compacted thereagainst, and integrally and permanently securing the second flange element to the first flange element around their respective outer peripheries; and providing a formed or pressure-formable aperture in the second flange element in substantial alignment with the formed or pressure-formable aperture in the first flange element, said second flange element aperture having a diameter smaller than the diameter of the main sheath portion, wherein said first flange element aperture diameter and second flange element aperture diameter are sized to compressively bear against the circumference of the member when sheathed in the article.

32. A method according to claim 31, wherein the compacted form of the sheath comprises a center-compacted form.

33. A method according to claim 31, wherein the compacted form of the sheath comprises a center-rolled form.

* * * * *

UNITED STATES PATENT AND TRADEMARK OFFICE
CERTIFICATE OF CORRECTION

PATENT NO. : 5,351,698
DATED : October 4, 1994
INVENTOR(S) : ROBERT G. WHEELER, ET AL.

It is certified that error appears in the above-indentified patent and that said Letters Patent is hereby corrected as shown below:

Column 1, line 26, insert the following information:

-- <u>GOVERNMENT LICENSE RIGHTS</u>

The invention claimed herein was made under one or more of the following contracts: U.S. Agency for International Development Contract Nos. DPE-3041-A-00-0043 and DPE-0537-A-00-4047, and National Institutes of Health Contract No. N01-HD-2-3143, and the U.S. government has certain rights therein. --

Signed and Sealed this

Fifteenth Day of November, 1994

Attest:

BRUCE LEHMAN

*Attesting Officer*     *Commissioner of Patents and Trademarks*